(12) United States Patent
Pioszak

(10) Patent No.: US 9,777,052 B2
(45) Date of Patent: Oct. 3, 2017

(54) R-SPONDIN VARIANTS, COMPOSITIONS, AND METHODS OF USE

(71) Applicant: The Board of Regents of the University of Oklahoma, Norman, OK (US)

(72) Inventor: Augen A. Pioszak, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 14/956,921

(22) Filed: Dec. 2, 2015

(65) Prior Publication Data

US 2016/0152947 A1 Jun. 2, 2016

Related U.S. Application Data

(60) Provisional application No. 62/086,484, filed on Dec. 2, 2014.

(51) Int. Cl.
*C07K 14/00* (2006.01)
*C07K 14/47* (2006.01)

(52) U.S. Cl.
CPC ...... *C07K 14/4705* (2013.01); *C07K 14/4702* (2013.01); *C07K 2319/00* (2013.01)

(58) Field of Classification Search
None
See application file for complete search history.

(56) References Cited

U.S. PATENT DOCUMENTS

| 8,642,339 | B2 | 2/2014 | Sato et al. |
| 2007/0059829 | A1 | 3/2007 | Yoon |
| 2013/0209473 | A1 | 8/2013 | de Sauvage et al. |

OTHER PUBLICATIONS

Moad and Pioszak, Biochemistry. Oct. 15, 2013; 52(41): 10.1021/bi401090h.*
Levin, et al.; "Exploiting a natural conformational switch to engineer an interleukin-2 'superkine'," Nature (2012), vol. 484, pp. 529-535.
Mahe, et al.; "Establishment of Gastrointestinal Epithelial Organoids," Current Protocols in Mouse Biology (2013), vol. 3 pp. 217-240.
Moad, et al.; "Reconstitution of R-Spondin:LGR4:ZNRF3 Adult Stem Cell Growth Factor Signaling Complexes with Recombinant Proteins Produced in *Escherichia coli*," Biochemistry (2013), vol. 52, pp. 7295-7304.
Warner, et al.; "Engineering High-Potency R-spondin Adult Stem Cell Growth Factors," Molecular Pharmacology (2015) vol. 87, pp. 410-420.
Chi, Kelly Rae; "Orchestrating Organoids," The Scientist Magazine (2015), pp. 1-6.
Willyard, Cassandra; "Rise of the Organoids," Nature (2015); vol. 523, pp. 520-522.
Sato, et al.; "Single Lgr5 stem cells build crypt-villus structures in vitro without a mesenchymal niche," Nature (2009), vol. 459, pp. 262-266.
Sato, et al.; Supplementary Information Nature (2009), vol. 459, pp. 1-9.
Sato, et al.; Supplementary Information; Nature (2009), vol. 459, pp. 1-9.
Takebe, et al.; "Vascularized and Complex Organ Buds from Diverse Tissue via Mesenchymal Cell-Driven Condensation," Cell Stem Cell, (2015), vol. 16, pp. 556-565.
Zebisch, et al.; "Structural and molecular basis of ZNRF3/RNF43 transmembrane ubiquitin ligase inhibition by the Wnt agonist R-spondin," Nature Communications, (2013), vol. 4, No. 2787, pp. 1-12.
Zebisch, et al.;Supplementary Figures, Nature Communications (2013), vol. 4, 14 pages.

* cited by examiner

*Primary Examiner* — Jeanette Lieb
(74) *Attorney, Agent, or Firm* — Dunlap Codding, P.C.

(57) ABSTRACT

R-spondin variants comprising a ZNRF3 binding region of a first R-spondin and an LGR4 binding region of a second R-spondin are disclosed. Cell culture media and compositions containing the R-spondin variants, as well as methods of their use, are also disclosed.

6 Claims, 19 Drawing Sheets
(13 of 19 Drawing Sheet(s) Filed in Color)

```
1           10         20         30         40         50
QGNRWRRSKRASYVSNPICKGCLSCSKDNGCSRCQQKLFFLRREGMRQYGECL 60         70         80         90        100
HDCPPGYFGIRGQEVNRCKKCGATCESCFSQDFCIRCKRQFYLYKGKCLPTCPPG
  S  S    Y  H  APDM      AR 110        120
TLAHQNTRECQGE
```

FIGURE 9

```
        1            10           20           30           40           50
QNASRGRRQRRMHPNVSQGCQGGCATCSDYNGCLSCKPRLFFALERIGMKQIG 60           70           80           90          100
VCLSDCPPGYFGIRGQEVNRCKKCGATCESCFSQDFCIRCKRQFYLYKGKCLPT
    S   S  Y T YPDI    T
                T 110          120
CPPGTLAHQNTRECQGE
```

FIGURE 10

SEQUENCE LISTING

```
<160> NUMBER OF SEQ ID NOS: 36

<210> SEQ ID NO 1
<211> LENGTH: 147
<212> TYPE: PRT
<213> ORGANISM: Homo sapiens

<400> SEQUENCE: 1

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln
145

<210> SEQ ID NO 2
<211> LENGTH: 144
<212> TYPE: PRT
<213> ORGANISM: Homo sapiens

<400> SEQUENCE: 2

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
```

```
                20              25              30
Ser Tyr Val Ser Asn Pro Ile Cys Lys Gly Cys Leu Ser Cys Ser Lys
                35              40              45

Asp Asn Gly Cys Ser Arg Cys Gln Gln Lys Leu Phe Phe Phe Leu Arg
                50              55              60

Arg Glu Gly Met Arg Gln Tyr Gly Glu Cys Leu His Ser Cys Pro Ser
65              70              75              80

Gly Tyr Tyr Gly His Arg Ala Pro Asp Met Asn Arg Cys Ala Arg Cys
                85              90              95

Arg Ile Glu Asn Cys Asp Ser Cys Phe Ser Lys Asp Phe Cys Thr Lys
                100             105             110

Cys Lys Val Gly Phe Tyr Leu His Arg Gly Arg Cys Phe Asp Glu Cys
                115             120             125

Pro Asp Gly Phe Ala Pro Leu Glu Glu Thr Met Glu Cys Val Glu Gly
                130             135             140

<210> SEQ ID NO 3
<211> LENGTH: 147
<212> TYPE: PRT
<213> ORGANISM: Homo sapiens

<400> SEQUENCE: 3

Met His Leu Arg Leu Ile Ser Trp Leu Phe Ile Ile Leu Asn Phe Met
1               5               10              15

Glu Tyr Ile Gly Ser Gln Asn Ala Ser Arg Gly Arg Gln Arg Arg
                20              25              30

Met His Pro Asn Val Ser Gln Gly Cys Gln Gly Gly Cys Ala Thr Cys
                35              40              45

Ser Asp Tyr Asn Gly Cys Leu Ser Cys Lys Pro Arg Leu Phe Phe Ala
                50              55              60

Leu Glu Arg Ile Gly Met Lys Gln Ile Gly Val Cys Leu Ser Ser Cys
65              70              75              80

Pro Ser Gly Tyr Tyr Gly Thr Arg Tyr Pro Asp Ile Asn Lys Cys Thr
                85              90              95

Lys Cys Lys Ala Asp Cys Asp Thr Cys Phe Asn Lys Asn Phe Cys Thr
                100             105             110

Lys Cys Lys Ser Gly Phe Tyr Leu His Leu Gly Lys Cys Leu Asp Asn
                115             120             125

Cys Pro Glu Gly Leu Glu Ala Asn Asn His Thr Met Glu Cys Val Ser
                130             135             140

Ile Val His
145

<210> SEQ ID NO 4
<211> LENGTH: 138
<212> TYPE: PRT
<213> ORGANISM: Homo sapiens

<400> SEQUENCE: 4

Met Arg Ala Pro Leu Cys Leu Leu Leu Leu Val Ala His Ala Val Asp
1               5               10              15

Met Leu Ala Leu Asn Arg Arg Lys Lys Gln Val Gly Thr Gly Leu Gly
                20              25              30

Gly Asn Cys Thr Gly Cys Ile Ile Cys Ser Glu Glu Asn Gly Cys Ser
                35              40              45

Thr Cys Gln Gln Arg Leu Phe Leu Phe Ile Arg Arg Glu Gly Ile Arg
```

```
                50              55                  60
Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
                100                 105                 110

Leu Tyr Lys Gly Lys Cys Leu Pro Thr Cys Pro Pro Gly Thr Leu Ala
                115                 120                 125

His Gln Asn Thr Arg Glu Cys Gln Gly Glu
                130                 135

<210> SEQ ID NO 5
<211> LENGTH: 506
<212> TYPE: PRT
<213> ORGANISM: Artificial sequence
<220> FEATURE:
<223> OTHER INFORMATION: MBP-Th-hRSPO1.21-145: human RSPO Fu1-Fu2
      construct as MBP-Thrombin cut site-RSPO Fu1-Fu2 fusion protein

<400> SEQUENCE: 5

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
                20                  25                  30

Thr Gly Ile Lys Val Thr Val Glu His Pro Asp Lys Leu Glu Glu Lys
                35                  40                  45

Phe Pro Gln Val Ala Ala Thr Gly Asp Gly Pro Asp Ile Ile Phe Trp
            50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
                100                 105                 110

Glu Ala Leu Ser Leu Ile Tyr Asn Lys Asp Leu Leu Pro Asn Pro Pro
                115                 120                 125

Lys Thr Trp Glu Glu Ile Pro Ala Leu Asp Lys Glu Leu Lys Ala Lys
                130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
                180                 185                 190

Gly Leu Thr Phe Leu Val Asp Leu Ile Lys Asn Lys His Met Asn Ala
                195                 200                 205

Asp Thr Asp Tyr Ser Ile Ala Glu Ala Ala Phe Asn Lys Gly Glu Thr
                210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
                260                 265                 270
```

```
Pro Asn Lys Glu Leu Ala Lys Glu Phe Leu Glu Asn Tyr Leu Leu Thr
            275                 280                 285

Asp Glu Gly Leu Glu Ala Val Asn Lys Asp Lys Pro Leu Gly Ala Val
        290                 295                 300

Ala Leu Lys Ser Tyr Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Gly Ser Ser Ser Gly Gly Leu Val Pro Arg Gly Ser Arg Gly
    370                 375                 380

Ile Lys Gly Lys Arg Gln Arg Ile Ser Ala Glu Gly Ser Gln Ala
385                 390                 395                 400

Cys Ala Lys Gly Cys Glu Leu Cys Ser Glu Val Asn Gly Cys Leu Lys
                405                 410                 415

Cys Ser Pro Lys Leu Phe Ile Leu Leu Glu Arg Asn Asp Ile Arg Gln
            420                 425                 430

Val Gly Val Cys Leu Pro Ser Cys Pro Pro Gly Tyr Phe Asp Ala Arg
        435                 440                 445

Asn Pro Asp Met Asn Lys Cys Ile Lys Cys Lys Ile Glu His Cys Glu
    450                 455                 460

Ala Cys Phe Ser His Asn Phe Cys Thr Lys Cys Lys Glu Gly Leu Tyr
465                 470                 475                 480

Leu His Lys Gly Arg Cys Tyr Pro Ala Cys Pro Glu Gly Ser Ser Ala
                485                 490                 495

Ala Asn Gly Thr Met Glu Cys Ser Ser Pro
            500                 505

<210> SEQ ID NO 6
<211> LENGTH: 504
<212> TYPE: PRT
<213> ORGANISM: Artificial sequence
<220> FEATURE:
<223> OTHER INFORMATION: MBP-Th-hRSPO2.22-144: human RSPO Fu1-Fu2
      construct as MBP-Thrombin cut site-RSPO Fu1-Fu2 fusion protein

<400> SEQUENCE: 6

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125
```

```
Lys Thr Trp Glu Glu Ile Pro Ala Leu Asp Lys Glu Leu Lys Ala Lys
            130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Gly Ser Ser Ser Gly Gly Leu Val Pro Arg Gly Ser Gln Gly Asn
    370                 375                 380

Arg Trp Arg Arg Ser Lys Arg Ala Ser Tyr Val Ser Asn Pro Ile Cys
385                 390                 395                 400

Lys Gly Cys Leu Ser Cys Ser Lys Asp Asn Gly Cys Ser Arg Cys Gln
                405                 410                 415

Gln Lys Leu Phe Phe Phe Leu Arg Arg Glu Gly Met Arg Gln Tyr Gly
            420                 425                 430

Glu Cys Leu His Ser Cys Pro Ser Gly Tyr Tyr Gly His Arg Ala Pro
        435                 440                 445

Asp Met Asn Arg Cys Ala Arg Cys Arg Ile Glu Asn Cys Asp Ser Cys
    450                 455                 460

Phe Ser Lys Asp Phe Cys Thr Lys Cys Lys Val Gly Phe Tyr Leu His
465                 470                 475                 480

Arg Gly Arg Cys Phe Asp Glu Cys Pro Asp Gly Phe Ala Pro Leu Glu
                485                 490                 495

Glu Thr Met Glu Cys Val Glu Gly
            500

<210> SEQ ID NO 7
<211> LENGTH: 506
<212> TYPE: PRT
<213> ORGANISM: Artificial sequence
<220> FEATURE:
```

<223> OTHER INFORMATION: MBP-Th-hRSPO3.22-146: human RSPO Fu1-Fu2
construct as MBP-Thrombin cut site-RSPO Fu1-Fu2 fusion protein

<400> SEQUENCE: 7

```
Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
290                 295                 300

Ala Leu Lys Ser Tyr Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Gly Ser Ser Ser Gly Gly Gly Leu Val Pro Arg Gly Ser Gln Asn Ala
370                 375                 380

Ser Arg Gly Arg Arg Gln Arg Arg Met His Pro Asn Val Ser Gln Gly
385                 390                 395                 400
```

```
Cys Gln Gly Gly Cys Ala Thr Cys Ser Asp Tyr Asn Gly Cys Leu Ser
                405                 410                 415

Cys Lys Pro Arg Leu Phe Phe Ala Leu Glu Arg Ile Gly Met Lys Gln
            420                 425                 430

Ile Gly Val Cys Leu Ser Ser Cys Pro Ser Gly Tyr Tyr Gly Thr Arg
        435                 440                 445

Tyr Pro Asp Ile Asn Lys Cys Thr Lys Cys Lys Ala Asp Cys Asp Thr
    450                 455                 460

Cys Phe Asn Lys Asn Phe Cys Thr Lys Cys Lys Ser Gly Phe Tyr Leu
465                 470                 475                 480

His Leu Gly Lys Cys Leu Asp Asn Cys Pro Glu Gly Leu Glu Ala Asn
            485                 490                 495

Asn His Thr Met Glu Cys Val Ser Ile Val
                500                 505

<210> SEQ ID NO 8
<211> LENGTH: 499
<212> TYPE: PRT
<213> ORGANISM: Artificial sequence
<220> FEATURE:
<223> OTHER INFORMATION: MBP-Th-hRSPO4.21-138:

<400> SEQUENCE: 8

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255
```

Ser Lys Pro Phe Val Gly Val Leu Ser Ala Gly Ile Asn Ala Ala Ser
               260                 265                 270

Pro Asn Lys Glu Leu Ala Lys Glu Phe Leu Glu Asn Tyr Leu Leu Thr
           275                 280                 285

Asp Glu Gly Leu Glu Ala Val Asn Lys Asp Lys Pro Leu Gly Ala Val
290                 295                 300

Ala Leu Lys Ser Tyr Glu Glu Leu Ala Lys Asp Pro Arg Ile Ala
305                 310                 315                 320

Ala Thr Met Glu Asn Ala Gln Lys Gly Glu Ile Met Pro Asn Ile Pro
               325                 330                 335

Gln Met Ser Ala Phe Trp Tyr Ala Val Arg Thr Ala Val Ile Asn Ala
           340                 345                 350

Ala Ser Gly Arg Gln Thr Val Asp Glu Ala Leu Lys Asp Ala Gln Thr
           355                 360                 365

Gly Ser Ser Ser Gly Gly Leu Val Pro Arg Gly Ser Asn Arg Arg
370                 375                 380

Lys Lys Gln Val Gly Thr Gly Leu Gly Gly Asn Cys Thr Gly Cys Ile
385                 390                 395                 400

Ile Cys Ser Glu Glu Asn Gly Cys Ser Thr Cys Gln Gln Arg Leu Phe
               405                 410                 415

Leu Phe Ile Arg Arg Glu Gly Ile Arg Gln Tyr Gly Lys Cys Leu His
           420                 425                 430

Asp Cys Pro Pro Gly Tyr Phe Gly Ile Arg Gly Gln Glu Val Asn Arg
           435                 440                 445

Cys Lys Lys Cys Gly Ala Thr Cys Glu Ser Cys Phe Ser Gln Asp Phe
           450                 455                 460

Cys Ile Arg Cys Lys Arg Gln Phe Tyr Leu Tyr Lys Gly Lys Cys Leu
465                 470                 475                 480

Pro Thr Cys Pro Pro Gly Thr Leu Ala His Gln Asn Thr Arg Glu Cys
               485                 490                 495

Gln Gly Glu

<210> SEQ ID NO 9
<211> LENGTH: 122
<212> TYPE: PRT
<213> ORGANISM: Artificial sequence
<220> FEATURE:
<223> OTHER INFORMATION: RSPO2-4 Fu1-Fu2 chimera: amino acids 22-76 of
      RSPO2 and amino acids 72-138 of RSPO4

<400> SEQUENCE: 9

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
               20                  25                  30

Arg Cys Gln Gln Lys Leu Phe Phe Leu Arg Arg Glu Gly Met Arg
           35                  40                  45

Gln Tyr Gly Glu Cys Leu His Asp Cys Pro Pro Gly Tyr Phe Gly Ile
           50                  55                  60

Arg Gly Gln Glu Val Asn Arg Cys Lys Lys Cys Gly Ala Thr Cys Glu
65                  70                  75                  80

Ser Cys Phe Ser Gln Asp Phe Cys Ile Arg Cys Lys Arg Gln Phe Tyr
               85                  90                  95

Leu Tyr Lys Gly Lys Cys Leu Pro Thr Cys Pro Pro Gly Thr Leu Ala
               100                 105                 110

His Gln Asn Thr Arg Glu Cys Gln Gly Glu
         115                 120

<210> SEQ ID NO 10
<211> LENGTH: 124
<212> TYPE: PRT
<213> ORGANISM: Artificial sequence
<220> FEATURE:
<223> OTHER INFORMATION: RSPO3-4 Fu1-Fu2 chimera: amino acids 22-78 of
      RSPO3 and amino acids 72-138 of RSPO4

<400> SEQUENCE: 10

Gln Asn Ala Ser Arg Gly Arg Arg Gln Arg Arg Met His Pro Asn Val
1               5                   10                  15

Ser Gln Gly Cys Gln Gly Gly Cys Ala Thr Cys Ser Asp Tyr Asn Gly
            20                  25                  30

Cys Leu Ser Cys Lys Pro Arg Leu Phe Phe Ala Leu Glu Arg Ile Gly
        35                  40                  45

Met Lys Gln Ile Gly Val Cys Leu Ser Asp Cys Pro Pro Gly Tyr Phe
    50                  55                  60

Gly Ile Arg Gly Gln Glu Val Asn Arg Cys Lys Lys Cys Gly Ala Thr
65                  70                  75                  80

Cys Glu Ser Cys Phe Ser Gln Asp Phe Cys Ile Arg Cys Lys Arg Gln
                85                  90                  95

Phe Tyr Leu Tyr Lys Gly Lys Cys Leu Pro Thr Cys Pro Pro Gly Thr
            100                 105                 110

Leu Ala His Gln Asn Thr Arg Glu Cys Gln Gly Glu
        115                 120

<210> SEQ ID NO 11
<211> LENGTH: 503
<212> TYPE: PRT
<213> ORGANISM: Artificial sequence
<220> FEATURE:
<223> OTHER INFORMATION: RSPO2-4 chimera: MBP-Thrombin cut
      site-RSPO2.22-76-RSPO4.72-138 fusion protein

<400> SEQUENCE: 11

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

```
Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Gly Ser Ser Ser Gly Gly Leu Val Pro Arg Gly Ser Gln Gly Asn
    370                 375                 380

Arg Trp Arg Arg Ser Lys Arg Ala Ser Tyr Val Ser Asn Pro Ile Cys
385                 390                 395                 400

Lys Gly Cys Leu Ser Cys Ser Lys Asp Asn Gly Cys Ser Arg Cys Gln
                405                 410                 415

Gln Lys Leu Phe Phe Phe Leu Arg Arg Glu Gly Met Arg Gln Tyr Gly
            420                 425                 430

Glu Cys Leu His Asp Cys Pro Pro Gly Tyr Phe Gly Ile Arg Gly Gln
        435                 440                 445

Glu Val Asn Arg Cys Lys Lys Cys Gly Ala Thr Cys Glu Ser Cys Phe
    450                 455                 460

Ser Gln Asp Phe Cys Ile Arg Cys Lys Arg Gln Phe Tyr Leu Tyr Lys
465                 470                 475                 480

Gly Lys Cys Leu Pro Thr Cys Pro Pro Gly Thr Leu Ala His Gln Asn
                485                 490                 495

Thr Arg Glu Cys Gln Gly Glu
            500

<210> SEQ ID NO 12
<211> LENGTH: 119
<212> TYPE: PRT
<213> ORGANISM: Artificial sequence
<220> FEATURE:
<223> OTHER INFORMATION: RSPO4-1 chimera: RSPO4 amino acids 21-71-RSPO-1
      amino acids 78-145

<400> SEQUENCE: 12

Asn Arg Arg Lys Lys Gln Val Gly Thr Gly Leu Gly Gly Asn Cys Thr
```

```
1               5                   10                  15
Gly Cys Ile Ile Cys Ser Glu Glu Asn Gly Cys Ser Thr Cys Gln Gln
                20                  25                  30

Arg Leu Phe Leu Phe Ile Arg Arg Glu Gly Ile Arg Gln Tyr Gly Lys
                35                  40                  45

Cys Leu His Ser Cys Pro Pro Gly Tyr Phe Asp Ala Arg Asn Pro Asp
                50                  55                  60

Met Asn Lys Cys Ile Lys Cys Lys Ile Glu His Cys Glu Ala Cys Phe
65              70                  75                  80

Ser His Asn Phe Cys Thr Lys Cys Lys Glu Gly Leu Tyr Leu His Lys
                85                  90                  95

Gly Arg Cys Tyr Pro Ala Cys Pro Glu Gly Ser Ser Ala Ala Asn Gly
                100                 105                 110

Thr Met Glu Cys Ser Ser Pro
                115

<210> SEQ ID NO 13
<211> LENGTH: 500
<212> TYPE: PRT
<213> ORGANISM: Artificial sequence
<220> FEATURE:
<223> OTHER INFORMATION: RSPO4-1 chimera: MBP-Thrombin cut
      site-RSPO4.21-71-RSPO1.78-145 fusion protein

<400> SEQUENCE: 13

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
                20                  25                  30

Thr Gly Ile Lys Val Thr Val Glu His Pro Asp Lys Leu Glu Glu Lys
                35                  40                  45

Phe Pro Gln Val Ala Ala Thr Gly Asp Gly Pro Asp Ile Ile Phe Trp
                50                  55                  60

Ala His Asp Arg Phe Gly Gly Tyr Ala Gln Ser Gly Leu Leu Ala Glu
65              70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
                100                 105                 110

Glu Ala Leu Ser Leu Ile Tyr Asn Lys Asp Leu Leu Pro Asn Pro Pro
                115                 120                 125

Lys Thr Trp Glu Glu Ile Pro Ala Leu Asp Lys Glu Leu Lys Ala Lys
                130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
                180                 185                 190

Gly Leu Thr Phe Leu Val Asp Leu Ile Lys Asn Lys His Met Asn Ala
                195                 200                 205

Asp Thr Asp Tyr Ser Ile Ala Glu Ala Ala Phe Asn Lys Gly Glu Thr
                210                 215                 220

Ala Met Thr Ile Asn Gly Pro Trp Ala Trp Ser Asn Ile Asp Thr Ser
225                 230                 235                 240
```

```
Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
            275                 280                 285

Asp Glu Gly Leu Glu Ala Val Asn Lys Asp Lys Pro Leu Gly Ala Val
        290                 295                 300

Ala Leu Lys Ser Tyr Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
            355                 360                 365

Gly Ser Ser Ser Gly Gly Leu Val Pro Arg Gly Ser Asn Arg Arg
        370                 375                 380

Lys Lys Gln Val Gly Thr Gly Leu Gly Gly Asn Cys Thr Gly Cys Ile
385                 390                 395                 400

Ile Cys Ser Glu Glu Asn Gly Cys Ser Thr Cys Gln Gln Arg Leu Phe
                405                 410                 415

Leu Phe Ile Arg Arg Glu Gly Ile Arg Gln Tyr Gly Lys Cys Leu His
            420                 425                 430

Ser Cys Pro Pro Gly Tyr Phe Asp Ala Arg Asn Pro Asp Met Asn Lys
            435                 440                 445

Cys Ile Lys Cys Lys Ile Glu His Cys Glu Ala Cys Phe Ser His Asn
450                 455                 460

Phe Cys Thr Lys Cys Lys Glu Gly Leu Tyr Leu His Lys Gly Arg Cys
465                 470                 475                 480

Tyr Pro Ala Cys Pro Glu Gly Ser Ala Ala Asn Gly Thr Met Glu
                485                 490                 495

Cys Ser Ser Pro
            500

<210> SEQ ID NO 14
<211> LENGTH: 118
<212> TYPE: PRT
<213> ORGANISM: Artificial sequence
<220> FEATURE:
<223> OTHER INFORMATION: RSPO4 Fu1-Fu2 [L56F/I58L/I63M] triple
      mutant - based on amino acids 21-138 of RSPO4

<400> SEQUENCE: 14

Asn Arg Arg Lys Lys Gln Val Gly Thr Gly Leu Gly Gly Asn Cys Thr
1               5                   10                  15

Gly Cys Ile Ile Cys Ser Glu Glu Asn Gly Cys Ser Thr Cys Gln Gln
            20                  25                  30

Arg Leu Phe Phe Phe Leu Arg Arg Glu Gly Met Arg Gln Tyr Gly Lys
        35                  40                  45

Cys Leu His Asp Cys Pro Pro Gly Tyr Phe Gly Ile Arg Gly Gln Glu
    50                  55                  60

Val Asn Arg Cys Lys Lys Cys Gly Ala Thr Cys Glu Ser Cys Phe Ser
65                  70                  75                  80

Gln Asp Phe Cys Ile Arg Cys Lys Arg Gln Phe Tyr Leu Tyr Lys Gly
                85                  90                  95
```

Lys Cys Leu Pro Thr Cys Pro Pro Gly Thr Leu Ala His Gln Asn Thr
                100                 105                 110

Arg Glu Cys Gln Gly Glu
        115

<210> SEQ ID NO 15
<211> LENGTH: 499
<212> TYPE: PRT
<213> ORGANISM: Artificial sequence
<220> FEATURE:
<223> OTHER INFORMATION: RSPO4 Fu1-Fu2 [L56F/I58L/I63M] triple mutant as
      MBP-Thrombin cut site-RSPO4.21-138 [L56F/I58L/I63M] fusion protein

<400> SEQUENCE: 15

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro

```
                    325                 330                 335

Gln Met Ser Ala Phe Trp Tyr Ala Val Arg Thr Ala Val Ile Asn Ala
                340                 345                 350

Ala Ser Gly Arg Gln Thr Val Asp Glu Ala Leu Lys Asp Ala Gln Thr
            355                 360                 365

Gly Ser Ser Gly Gly Gly Leu Val Pro Arg Gly Ser Asn Arg Arg
        370                 375                 380

Lys Lys Gln Val Gly Thr Gly Leu Gly Gly Asn Cys Thr Gly Cys Ile
385                 390                 395                 400

Ile Cys Ser Glu Glu Asn Gly Cys Ser Thr Cys Gln Gln Arg Leu Phe
                405                 410                 415

Phe Phe Leu Arg Arg Glu Gly Met Arg Gln Tyr Gly Lys Cys Leu His
                420                 425                 430

Asp Cys Pro Pro Gly Tyr Phe Gly Ile Arg Gly Gln Glu Val Asn Arg
            435                 440                 445

Cys Lys Lys Cys Gly Ala Thr Cys Glu Ser Cys Phe Ser Gln Asp Phe
        450                 455                 460

Cys Ile Arg Cys Lys Arg Gln Phe Tyr Leu Tyr Lys Gly Lys Cys Leu
465                 470                 475                 480

Pro Thr Cys Pro Pro Gly Thr Leu Ala His Gln Asn Thr Arg Glu Cys
                485                 490                 495

Gln Gly Glu

<210> SEQ ID NO 16
<211> LENGTH: 123
<212> TYPE: PRT
<213> ORGANISM: Artificial sequence
<220> FEATURE:
<223> OTHER INFORMATION: RSPO2 Fu1-Fu2 [T111I] single mutant

<400> SEQUENCE: 16

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Ser Cys Pro Ser Gly Tyr Tyr Gly His
    50                  55                  60

Arg Ala Pro Asp Met Asn Arg Cys Ala Arg Cys Arg Ile Glu Asn Cys
65                  70                  75                  80

Asp Ser Cys Phe Ser Lys Asp Phe Cys Ile Lys Cys Lys Val Gly Phe
                85                  90                  95

Tyr Leu His Arg Gly Arg Cys Phe Asp Glu Cys Pro Asp Gly Phe Ala
            100                 105                 110

Pro Leu Glu Glu Thr Met Glu Cys Val Glu Gly
        115                 120

<210> SEQ ID NO 17
<211> LENGTH: 125
<212> TYPE: PRT
<213> ORGANISM: Artificial sequence
<220> FEATURE:
<223> OTHER INFORMATION: RSPO3 Fu1-Fu2 [T112I] single mutant

<400> SEQUENCE: 17

Gln Asn Ala Ser Arg Gly Arg Arg Gln Arg Arg Met His Pro Asn Val
```

```
                1               5              10              15
            Ser Gln Gly Cys Gln Gly Gly Cys Ala Thr Cys Ser Asp Tyr Asn Gly
                           20              25              30

Cys Leu Ser Cys Lys Pro Arg Leu Phe Phe Ala Leu Glu Arg Ile Gly
                           35              40              45

Met Lys Gln Ile Gly Val Cys Leu Ser Ser Cys Pro Ser Gly Tyr Tyr
                 50              55              60

Gly Thr Arg Tyr Pro Asp Ile Asn Lys Cys Thr Lys Cys Lys Ala Asp
            65              70              75              80

Cys Asp Thr Cys Phe Asn Lys Asn Phe Cys Ile Lys Cys Lys Ser Gly
                           85              90              95

Phe Tyr Leu His Leu Gly Lys Cys Leu Asp Asn Cys Pro Glu Gly Leu
                          100             105             110

Glu Ala Asn Asn His Thr Met Glu Cys Val Ser Ile Val
                          115             120             125
```

<210> SEQ ID NO 18
<211> LENGTH: 562
<212> TYPE: PRT
<213> ORGANISM: Artificial sequence
<220> FEATURE:
<223> OTHER INFORMATION: Human ZNRF3 ECD construct used for binary and
      ternary complex AlphaLISA binding assays suitable for
      high-throughput drug screening. As MBP-Thrombin cut
      site-Biotinylation Avi tag-ZNRF3.56-216 fusion protein.

<400> SEQUENCE: 18

```
            Met Ala Lys Ile Glu Glu Gly Lys Leu Val Ile Trp Ile Asn Gly Asp
            1               5              10              15

Lys Gly Tyr Asn Gly Leu Ala Glu Val Gly Lys Lys Phe Glu Lys Asp
                           20              25              30

Thr Gly Ile Lys Val Thr Val Glu His Pro Asp Lys Leu Glu Glu Lys
                           35              40              45

Phe Pro Gln Val Ala Ala Thr Gly Asp Gly Pro Asp Ile Ile Phe Trp
                 50              55              60

Ala His Asp Arg Phe Gly Gly Tyr Ala Gln Ser Gly Leu Leu Ala Glu
            65              70              75              80

Ile Thr Pro Asp Lys Ala Phe Gln Asp Lys Leu Tyr Pro Phe Thr Trp
                           85              90              95

Asp Ala Val Arg Tyr Asn Gly Lys Leu Ile Ala Tyr Pro Ile Ala Val
                          100             105             110

Glu Ala Leu Ser Leu Ile Tyr Asn Lys Asp Leu Leu Pro Asn Pro Pro
                          115             120             125

Lys Thr Trp Glu Glu Ile Pro Ala Leu Asp Lys Glu Leu Lys Ala Lys
                          130             135             140

Gly Lys Ser Ala Leu Met Phe Asn Leu Gln Glu Pro Tyr Phe Thr Trp
            145                 150             155             160

Pro Leu Ile Ala Ala Asp Gly Gly Tyr Ala Phe Lys Tyr Glu Asn Gly
                          165             170             175

Lys Tyr Asp Ile Lys Asp Val Gly Val Asp Asn Ala Gly Ala Lys Ala
                          180             185             190

Gly Leu Thr Phe Leu Val Asp Leu Ile Lys Asn Lys His Met Asn Ala
                          195             200             205

Asp Thr Asp Tyr Ser Ile Ala Glu Ala Ala Phe Asn Lys Gly Glu Thr
                          210             215             220

Ala Met Thr Ile Asn Gly Pro Trp Ala Trp Ser Asn Ile Asp Thr Ser
```

```
            225                 230                 235                 240
Lys Val Asn Tyr Gly Val Thr Val Leu Pro Thr Phe Lys Gly Gln Pro
                245                 250                 255
Ser Lys Pro Phe Val Gly Val Leu Ser Ala Gly Ile Asn Ala Ala Ser
                260                 265                 270
Pro Asn Lys Glu Leu Ala Lys Glu Phe Leu Glu Asn Tyr Leu Leu Thr
                275                 280                 285
Asp Glu Gly Leu Glu Ala Val Asn Lys Asp Lys Pro Leu Gly Ala Val
                290                 295                 300
Ala Leu Lys Ser Tyr Glu Glu Glu Leu Ala Lys Asp Pro Arg Ile Ala
305                 310                 315                 320
Ala Thr Met Glu Asn Ala Gln Lys Gly Glu Ile Met Pro Asn Ile Pro
                325                 330                 335
Gln Met Ser Ala Phe Trp Tyr Ala Val Arg Thr Ala Val Ile Asn Ala
                340                 345                 350
Ala Ser Gly Arg Gln Thr Val Asp Glu Ala Leu Lys Asp Ala Gln Thr
                355                 360                 365
Gly Ser Ser Ser Gly Gly Leu Val Pro Arg Gly Ser Gly Gly Leu
                370                 375                 380
Asn Asp Ile Phe Glu Ala Gln Lys Ile Glu Trp His Glu Asp Thr Gly
385                 390                 395                 400
Ser Lys Glu Thr Ala Phe Val Glu Val Leu Phe Glu Ser Ser Pro
                405                 410                 415
Ser Gly Asp Tyr Thr Thr Tyr Thr Thr Gly Leu Thr Gly Arg Phe Ser
                420                 425                 430
Arg Ala Gly Ala Thr Leu Ser Ala Glu Gly Glu Ile Val Gln Met His
                435                 440                 445
Pro Leu Gly Leu Cys Asn Asn Asn Asp Glu Glu Asp Leu Tyr Glu Tyr
                450                 455                 460
Gly Trp Val Gly Val Val Lys Leu Glu Gln Pro Glu Leu Asp Pro Lys
465                 470                 475                 480
Pro Cys Leu Thr Val Leu Gly Lys Ala Lys Arg Ala Val Gln Arg Gly
                485                 490                 495
Ala Thr Ala Val Ile Phe Asp Val Ser Glu Asn Pro Glu Ala Ile Asp
                500                 505                 510
Gln Leu Asn Gln Gly Ser Glu Asp Pro Leu Lys Arg Pro Val Val Tyr
                515                 520                 525
Val Lys Gly Ala Asp Ala Ile Lys Leu Met Asn Ile Val Asn Lys Gln
                530                 535                 540
Lys Val Ala Arg Ala Arg Ile Gln His Arg Pro Pro Arg Gln Pro Thr
545                 550                 555                 560
Glu Tyr

<210> SEQ ID NO 19
<211> LENGTH: 742
<212> TYPE: PRT
<213> ORGANISM: Artificial sequence
<220> FEATURE:
<223> OTHER INFORMATION: Human LGR4 LRR1-14 ECD construct used for
      ternary complex AlphaLISA binding assay suitable for
      high-throughput drug screening. As MBP-Thrombin cut
      site-LGR4.23-383 fusion protein

<400> SEQUENCE: 19

Met Ala Lys Ile Glu Glu Gly Lys Leu Val Ile Trp Ile Asn Gly Asp
1               5                   10                  15
```

```
Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
            35                  40                  45

Phe Pro Gln Val Ala Ala Thr Gly Asp Gly Pro Asp Ile Ile Phe Trp
 50                  55                  60

Ala His Asp Arg Phe Gly Gly Tyr Ala Gln Ser Gly Leu Leu Ala Glu
 65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
                100                 105                 110

Glu Ala Leu Ser Leu Ile Tyr Asn Lys Asp Leu Leu Pro Asn Pro Pro
            115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
                180                 185                 190

Gly Leu Thr Phe Leu Val Asp Leu Ile Lys Asn Lys His Met Asn Ala
            195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
                260                 265                 270

Pro Asn Lys Glu Leu Ala Lys Glu Phe Leu Glu Asn Tyr Leu Leu Thr
            275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
                340                 345                 350

Ala Ser Gly Arg Gln Thr Val Asp Glu Ala Leu Lys Asp Ala Gln Thr
            355                 360                 365

Gly Ser Ser Ser Gly Gly Leu Val Pro Arg Gly Ser Gly Ala Ala
    370                 375                 380

Pro Pro Leu Cys Ala Ala Pro Cys Ser Cys Asp Gly Asp Arg Arg Val
385                 390                 395                 400

Asp Cys Ser Gly Lys Gly Leu Thr Ala Val Pro Glu Gly Leu Ser Ala
                405                 410                 415

Phe Thr Gln Ala Leu Asp Ile Ser Met Asn Asn Ile Thr Gln Leu Pro
                420                 425                 430
```

```
Glu Asp Ala Phe Lys Asn Phe Pro Phe Leu Glu Leu Gln Leu Ala
            435                 440                 445
Gly Asn Asp Leu Ser Phe Ile His Pro Lys Ala Leu Ser Gly Leu Lys
450                 455                 460
Glu Leu Lys Val Leu Thr Leu Gln Asn Asn Gln Leu Lys Thr Val Pro
465                 470                 475                 480
Ser Glu Ala Ile Arg Gly Leu Ser Ala Leu Gln Ser Leu Arg Leu Asp
                485                 490                 495
Ala Asn His Ile Thr Ser Val Pro Glu Asp Ser Phe Glu Gly Leu Val
            500                 505                 510
Gln Leu Arg His Leu Trp Leu Asp Asp Asn Ser Leu Thr Glu Val Pro
        515                 520                 525
Val His Pro Leu Ser Asn Leu Pro Thr Leu Gln Ala Leu Thr Leu Ala
    530                 535                 540
Leu Asn Lys Ile Ser Ser Ile Pro Asp Phe Ala Phe Thr Asn Leu Ser
545                 550                 555                 560
Ser Leu Val Val Leu His Leu His Asn Asn Lys Ile Arg Ser Leu Ser
                565                 570                 575
Gln His Cys Phe Asp Gly Leu Asp Asn Leu Glu Thr Leu Asp Leu Asn
            580                 585                 590
Tyr Asn Asn Leu Gly Glu Phe Pro Gln Ala Ile Lys Ala Leu Pro Ser
        595                 600                 605
Leu Lys Glu Leu Gly Phe His Ser Asn Ser Ile Ser Val Ile Pro Asp
    610                 615                 620
Gly Ala Phe Asp Gly Asn Pro Leu Leu Arg Thr Ile His Leu Tyr Asp
625                 630                 635                 640
Asn Pro Leu Ser Phe Val Gly Asn Ser Ala Phe His Asn Leu Ser Asp
                645                 650                 655
Leu His Ser Leu Val Ile Arg Gly Ala Ser Met Val Gln Gln Phe Pro
            660                 665                 670
Asn Leu Thr Gly Thr Val His Leu Glu Ser Leu Thr Leu Thr Gly Thr
        675                 680                 685
Lys Ile Ser Ser Ile Pro Asn Asn Leu Cys Gln Glu Gln Lys Met Leu
    690                 695                 700
Arg Thr Leu Asp Leu Ser Tyr Asn Asn Ile Arg Asp Leu Pro Ser Phe
705                 710                 715                 720
Asn Gly Cys His Ala Leu Glu Glu Ile Ser Leu Gln Arg Asn Gln Ile
                725                 730                 735
Tyr Gln Ile Lys Glu Gly
            740

<210> SEQ ID NO 20
<211> LENGTH: 62
<212> TYPE: PRT
<213> ORGANISM: Homo sapiens

<400> SEQUENCE: 20

Cys Glu Met Ser Glu Trp Ser Pro Trp Gly Pro Cys Ser Lys Lys Gln
1               5                   10                  15
Gln Leu Cys Gly Phe Arg Arg Gly Ser Glu Glu Arg Thr Arg Arg Val
            20                  25                  30
Leu His Ala Pro Val Gly Asp His Ala Ala Cys Ser Asp Thr Lys Glu
        35                  40                  45
Thr Arg Arg Cys Thr Val Arg Arg Val Pro Cys Pro Glu Gly
    50                  55                  60
```

<210> SEQ ID NO 21
<211> LENGTH: 62
<212> TYPE: PRT
<213> ORGANISM: Homo sapiens

<400> SEQUENCE: 21

```
Cys Glu Val Gly His Trp Ser Glu Trp Gly Thr Cys Ser Arg Asn Asn
1               5                   10                  15

Arg Thr Cys Gly Phe Lys Trp Gly Leu Glu Thr Arg Thr Arg Gln Ile
            20                  25                  30

Val Lys Lys Pro Val Lys Asp Thr Ile Leu Cys Pro Thr Ile Ala Glu
        35                  40                  45

Ser Arg Arg Cys Lys Met Thr Met Arg His Cys Pro Gly Gly
    50                  55                  60
```

<210> SEQ ID NO 22
<211> LENGTH: 62
<212> TYPE: PRT
<213> ORGANISM: Homo sapiens

<400> SEQUENCE: 22

```
Cys Glu Val Ser Glu Trp Asn Pro Trp Ser Pro Cys Thr Lys Lys Gly
1               5                   10                  15

Lys Thr Cys Gly Phe Lys Arg Gly Thr Glu Thr Arg Val Arg Glu Ile
            20                  25                  30

Ile Gln His Pro Ser Ala Lys Gly Asn Leu Cys Pro Pro Thr Asn Glu
        35                  40                  45

Thr Arg Lys Cys Thr Val Gln Arg Lys Lys Cys Gln Lys Gly
    50                  55                  60
```

<210> SEQ ID NO 23
<211> LENGTH: 54
<212> TYPE: PRT
<213> ORGANISM: Homo sapiens

<400> SEQUENCE: 23

```
Gln Lys Arg Arg Lys Gly Gly Gln Gly Arg Glu Asn Ala Asn Arg
1               5                   10                  15

Asn Leu Ala Arg Lys Glu Ser Lys Glu Ala Gly Ala Gly Ser Arg Arg
            20                  25                  30

Arg Lys Gly Gln Gln Gln Gln Gln Gln Gly Thr Val Gly Pro Leu
        35                  40                  45

Thr Ser Ala Gly Pro Ala
    50
```

<210> SEQ ID NO 24
<211> LENGTH: 62
<212> TYPE: PRT
<213> ORGANISM: Homo sapiens

<400> SEQUENCE: 24

```
Glu Arg Gly Lys Lys Gly Arg Glu Arg Lys Arg Lys Lys Pro Asn Lys
1               5                   10                  15

Gly Glu Ser Lys Glu Ala Ile Pro Asp Ser Lys Ser Leu Glu Ser Ser
            20                  25                  30

Lys Glu Ile Pro Glu Gln Arg Glu Asn Lys Gln Gln Lys Lys Arg
        35                  40                  45

Lys Val Gln Asp Lys Gln Lys Ser Val Ser Val Ser Thr Val
```

<210> SEQ ID NO 25
<211> LENGTH: 184
<212> TYPE: PRT
<213> ORGANISM: Artificial sequence
<220> FEATURE:
<223> OTHER INFORMATION: RSPO2-4 Fu1-Fu2-TSP2 chimera: amino acids 22-76 of RSPO2 - amino acids 72-138 of RSPO4 - amino acids 145-206 of RSPO2

<400> SEQUENCE: 25

```
Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Asp Cys Pro Pro Gly Tyr Phe Gly Ile
    50                  55                  60

Arg Gly Gln Glu Val Asn Arg Cys Lys Lys Cys Gly Ala Thr Cys Glu
65                  70                  75                  80

Ser Cys Phe Ser Gln Asp Phe Cys Ile Arg Cys Lys Arg Gln Phe Tyr
                85                  90                  95

Leu Tyr Lys Gly Lys Cys Leu Pro Thr Cys Pro Pro Gly Thr Leu Ala
            100                 105                 110

His Gln Asn Thr Arg Glu Cys Gln Gly Glu Cys Glu Val Gly His Trp
        115                 120                 125

Ser Glu Trp Gly Thr Cys Ser Arg Asn Asn Arg Thr Cys Gly Phe Lys
    130                 135                 140

Trp Gly Leu Glu Thr Arg Thr Arg Gln Ile Val Lys Lys Pro Val Lys
145                 150                 155                 160

Asp Thr Ile Leu Cys Pro Thr Ile Ala Glu Ser Arg Arg Cys Lys Met
                165                 170                 175

Thr Met Arg His Cys Pro Gly Gly
            180
```

<210> SEQ ID NO 26
<211> LENGTH: 184
<212> TYPE: PRT
<213> ORGANISM: Artificial sequence
<220> FEATURE:
<223> OTHER INFORMATION: RSPO2-4 Fu1-Fu2-TSP1 chimera: amino acids 22-76 of RSPO2 - amino acids 72-138 of RSPO4 - amino acids 148-209 of RSPO1

<400> SEQUENCE: 26

```
Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Asp Cys Pro Pro Gly Tyr Phe Gly Ile
    50                  55                  60

Arg Gly Gln Glu Val Asn Arg Cys Lys Lys Cys Gly Ala Thr Cys Glu
65                  70                  75                  80

Ser Cys Phe Ser Gln Asp Phe Cys Ile Arg Cys Lys Arg Gln Phe Tyr
                85                  90                  95
```

```
Leu Tyr Lys Gly Lys Cys Leu Pro Thr Cys Pro Pro Gly Thr Leu Ala
            100                 105                 110

His Gln Asn Thr Arg Glu Cys Gln Gly Glu Cys Glu Met Ser Glu Trp
            115                 120                 125

Ser Pro Trp Gly Pro Cys Ser Lys Lys Gln Leu Cys Gly Phe Arg
            130                 135             140

Arg Gly Ser Glu Glu Arg Thr Arg Arg Val Leu His Ala Pro Val Gly
145                 150                 155                 160

Asp His Ala Ala Cys Ser Asp Thr Lys Glu Thr Arg Arg Cys Thr Val
                165                 170                 175

Arg Arg Val Pro Cys Pro Glu Gly
            180

<210> SEQ ID NO 27
<211> LENGTH: 184
<212> TYPE: PRT
<213> ORGANISM: Artificial sequence
<220> FEATURE:
<223> OTHER INFORMATION: RSPO2-4 Fu1-Fu2-TSP3 chimera: amino acids 22-76
      of RSPO2 - amino acids 72-138 of RSPO4 - amino acids 148-208 of
      RSPO3

<400> SEQUENCE: 27

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Leu Arg Arg Glu Gly Met Arg
            35                  40                  45

Gln Tyr Gly Glu Cys Leu His Asp Cys Pro Pro Gly Tyr Phe Gly Ile
50                  55                  60

Arg Gly Gln Glu Val Asn Arg Cys Lys Lys Cys Gly Ala Thr Cys Glu
65                  70                  75                  80

Ser Cys Phe Ser Gln Asp Phe Cys Ile Arg Cys Lys Arg Gln Phe Tyr
                85                  90                  95

Leu Tyr Lys Gly Lys Cys Leu Pro Thr Cys Pro Pro Gly Thr Leu Ala
            100                 105                 110

His Gln Asn Thr Arg Glu Cys Gln Gly Glu Cys Glu Val Ser Glu Trp
            115                 120                 125

Asn Pro Trp Ser Pro Cys Thr Lys Lys Gly Lys Thr Cys Gly Phe Lys
            130                 135             140

Arg Gly Thr Glu Thr Arg Val Arg Glu Ile Ile Gln His Pro Ser Ala
145                 150                 155                 160

Lys Gly Asn Leu Cys Pro Pro Thr Asn Glu Thr Arg Lys Cys Thr Val
                165                 170                 175

Gln Arg Lys Lys Cys Gln Lys Gly
            180

<210> SEQ ID NO 28
<211> LENGTH: 238
<212> TYPE: PRT
<213> ORGANISM: Artificial sequence
<220> FEATURE:
<223> OTHER INFORMATION: RSPO2-4 Fu1-Fu2-TSP1-basic region chimera:
      amino acids 22-76 of RSPO2 - amino acids 72-138 of RSPO4 - amino
      acids 148-263 of RSPO1

<400> SEQUENCE: 28
```

```
Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Asp Cys Pro Pro Gly Tyr Phe Gly Ile
    50                  55                  60

Arg Gly Gln Glu Val Asn Arg Cys Lys Lys Cys Gly Ala Thr Cys Glu
65                  70                  75                  80

Ser Cys Phe Ser Gln Asp Phe Cys Ile Arg Cys Lys Arg Gln Phe Tyr
                85                  90                  95

Leu Tyr Lys Gly Lys Cys Leu Pro Thr Cys Pro Pro Gly Thr Leu Ala
            100                 105                 110

His Gln Asn Thr Arg Glu Cys Gln Gly Glu Cys Glu Met Ser Glu Trp
        115                 120                 125

Ser Pro Trp Gly Pro Cys Ser Lys Lys Gln Gln Leu Cys Gly Phe Arg
    130                 135                 140

Arg Gly Ser Glu Glu Arg Thr Arg Arg Val Leu His Ala Pro Val Gly
145                 150                 155                 160

Asp His Ala Ala Cys Ser Asp Thr Lys Glu Thr Arg Arg Cys Thr Val
                165                 170                 175

Arg Arg Val Pro Cys Pro Glu Gly Gln Lys Arg Arg Lys Gly Gly Gln
            180                 185                 190

Gly Arg Arg Glu Asn Ala Asn Arg Asn Leu Ala Arg Lys Glu Ser Lys
        195                 200                 205

Glu Ala Gly Ala Gly Ser Arg Arg Arg Lys Gly Gln Gln Gln Gln Gln
    210                 215                 220

Gln Gln Gly Thr Val Gly Pro Leu Thr Ser Ala Gly Pro Ala
225                 230                 235

<210> SEQ ID NO 29
<211> LENGTH: 246
<212> TYPE: PRT
<213> ORGANISM: Artificial sequence
<220> FEATURE:
<223> OTHER INFORMATION: RSPO2-4 Fu1-Fu2-TSP3-basic region chimera:
      amino acids 22-76 of RSPO2 - amino acids 72-138 of RSPO4 - amino
      acids 148-272 of RSPO3

<400> SEQUENCE: 29

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Asp Cys Pro Pro Gly Tyr Phe Gly Ile
    50                  55                  60

Arg Gly Gln Glu Val Asn Arg Cys Lys Lys Cys Gly Ala Thr Cys Glu
65                  70                  75                  80

Ser Cys Phe Ser Gln Asp Phe Cys Ile Arg Cys Lys Arg Gln Phe Tyr
                85                  90                  95

Leu Tyr Lys Gly Lys Cys Leu Pro Thr Cys Pro Pro Gly Thr Leu Ala
            100                 105                 110

His Gln Asn Thr Arg Glu Cys Gln Gly Glu Cys Glu Val Ser Glu Trp
```

```
            115                 120                 125
Asn Pro Trp Ser Pro Cys Thr Lys Lys Gly Lys Thr Cys Gly Phe Lys
    130                 135                 140

Arg Gly Thr Glu Thr Arg Val Arg Glu Ile Ile Gln His Pro Ser Ala
145                 150                 155                 160

Lys Gly Asn Leu Cys Pro Pro Thr Asn Glu Thr Arg Lys Cys Thr Val
                165                 170                 175

Gln Arg Lys Lys Cys Gln Lys Gly Glu Arg Gly Lys Lys Gly Arg Glu
            180                 185                 190

Arg Lys Arg Lys Lys Pro Asn Lys Gly Glu Ser Lys Glu Ala Ile Pro
        195                 200                 205

Asp Ser Lys Ser Leu Glu Ser Ser Lys Glu Ile Pro Glu Gln Arg Glu
    210                 215                 220

Asn Lys Gln Gln Gln Lys Lys Arg Lys Val Gln Asp Lys Gln Lys Ser
225                 230                 235                 240

Val Ser Val Ser Thr Val
                245

<210> SEQ ID NO 30
<211> LENGTH: 6
<212> TYPE: PRT
<213> ORGANISM: Artificial sequence
<220> FEATURE:
<223> OTHER INFORMATION: H6 purification tag

<400> SEQUENCE: 30

His His His His His His
1               5

<210> SEQ ID NO 31
<211> LENGTH: 8
<212> TYPE: PRT
<213> ORGANISM: Artificial sequence
<220> FEATURE:
<223> OTHER INFORMATION: purification tag

<400> SEQUENCE: 31

Met Lys His His His His His His
1               5

<210> SEQ ID NO 32
<211> LENGTH: 10
<212> TYPE: PRT
<213> ORGANISM: Artificial sequence
<220> FEATURE:
<223> OTHER INFORMATION: purification tag

<400> SEQUENCE: 32

Met Lys His His Ala His His Gln His His
1               5                   10

<210> SEQ ID NO 33
<211> LENGTH: 14
<212> TYPE: PRT
<213> ORGANISM: Artificial sequence
<220> FEATURE:
<223> OTHER INFORMATION: purification tag

<400> SEQUENCE: 33

Met Leu His Gln His Gln His Gln His Gln His Gln
1               5                   10
```

```
<210> SEQ ID NO 34
<211> LENGTH: 10
<212> TYPE: PRT
<213> ORGANISM: Artificial sequence
<220> FEATURE:
<223> OTHER INFORMATION: purification tag

<400> SEQUENCE: 34

Glu Gln Lys Leu Ile Ser Glu Glu Asp Leu
1               5                   10

<210> SEQ ID NO 35
<211> LENGTH: 8
<212> TYPE: PRT
<213> ORGANISM: Artificial sequence
<220> FEATURE:
<223> OTHER INFORMATION: purification tag

<400> SEQUENCE: 35

Asp Tyr Lys Asp Asp Asp Asp Lys
1               5

<210> SEQ ID NO 36
<211> LENGTH: 9
<212> TYPE: PRT
<213> ORGANISM: Artificial sequence
<220> FEATURE:
<223> OTHER INFORMATION: purification tag

<400> SEQUENCE: 36

Tyr Pro Tyr Asp Val Pro Asp Tyr Ala
1               5
```

R-SPONDIN VARIANTS, COMPOSITIONS, AND METHODS OF USE

CROSS REFERENCE TO RELATED APPLICATIONS/INCORPORATION BY REFERENCE STATEMENT

This application claims benefit under 35 USC §119(e) of Provisional Application U.S. Ser. No. 62/086,484, filed Dec. 2, 2014, the entirety of which is hereby expressly incorporated herein by reference.

STATEMENT REGARDING FEDERALLY SPONSORED RESEARCH OR DEVELOPMENT

Not Applicable.

BACKGROUND

R-spondins-1-4 (RSPO1, RSPO2, RSPO3, and RSPO4) are secreted glycoproteins that potentiate Wnt signaling in vertebrates. RSPO actions are crucial for development and adult tissue homeostasis, and aberrant RSPO signaling is implicated in cancer. RSPOs are best characterized as growth factors for adult stem cells of the small intestine. Culture systems that permit in vitro growth of intestinal organoids from adult stem cells are dependent on exogenous RSPO1. RSPOs are thus valuable for regenerative medicine applications. Exogenous RSPO1 administration alleviated colitis symptoms in a mouse model and provided protection against chemo- and radiation therapy-induced tissue damage in mice.

RSPOs contain an N-terminal signal peptide followed by two cysteine-rich Furin-like domains, Fu1 and Fu2, a thrombospondin (TSP) domain, and a C-terminal basic region. The Fu1-Fu2 domain module is minimally sufficient to potentiate Wnt signaling. RSPOs signal through the leucine-rich repeat G protein-coupled receptors (GPCRs) LGR4-6 and the transmembrane E3 ubiquitin ligases ZNRF3 and RNF43. LGR5 marks intestinal adult stem cells. LGR4 is broadly expressed, but its co-expression with LGR5 in intestinal stem cells is crucial for their proliferation and crypt formation. RSPOs do not appear to activate classical GPCR signaling pathways; instead, RSPOs regulate Wnt receptor availability. ZNRF3/RNF43 ubiquitinate Frizzled Wnt receptors to cause their internalization and degradation. RSPOs inhibit ZNRF3/RNF43 by forming a ternary complex with LGR4/5/6 and ZNRF3/RNF43, which leads to membrane clearance of the E3 ligase and thereby more Wnt receptors at the cell surface. LGR4/5/6 have a large extracellular domain (ECD) with seventeen leucine rich-repeats (LRR) that provides the RSPO binding site, and ZNRF3/RNF43 have a small ECD for RSPO binding. Crystal structures of binary and ternary complexes and mutagenesis studies indicated that distinct regions of RSPO Fu1-Fu2 contact the two receptors.

All four RSPOs signal by a common mechanism and can promote the growth of intestinal stem cells, but significant functional differences exist. Genetic studies revealed roles for RSPO1-RSPO4 in sex determination, limb formation, placental development, and formation of toe- and fingernails, respectively. In cell-based Wnt signaling assays, RSPO2 and -3 were more active than RSPO1 and -4, and RSPO4 is considered the least active RSPO. The RSPOs bind LGRs with nM binding affinities, but conflicting results were reported for the rank order of RSPO1-RSPO4 binding to LGR4. RSPO2 and RSPO3 bound ZNRF3 with nM affinities, whereas RSPO1 and RSPO4 had affinities in the M range with RSPO4 having the weakest ZNRF3 binding.

Novel high-potency versions of RSPOs would be of value for regenerative medicine and/or therapeutic applications. It is to such novel R-spondins that the present disclosure is directed.

BRIEF DESCRIPTION OF THE DRAWINGS

Several embodiments of the present disclosure are hereby illustrated in the appended drawings. It is to be noted, however, that the appended drawings only illustrate several typical embodiments and are therefore not intended to be considered limiting of the scope of the present disclosure.

This patent or application file contains at least one drawing executed in color. Copies of this patent or patent application publication with color drawing(s) will be provided by the Office upon request and payment of the necessary fee.

Figure 4:
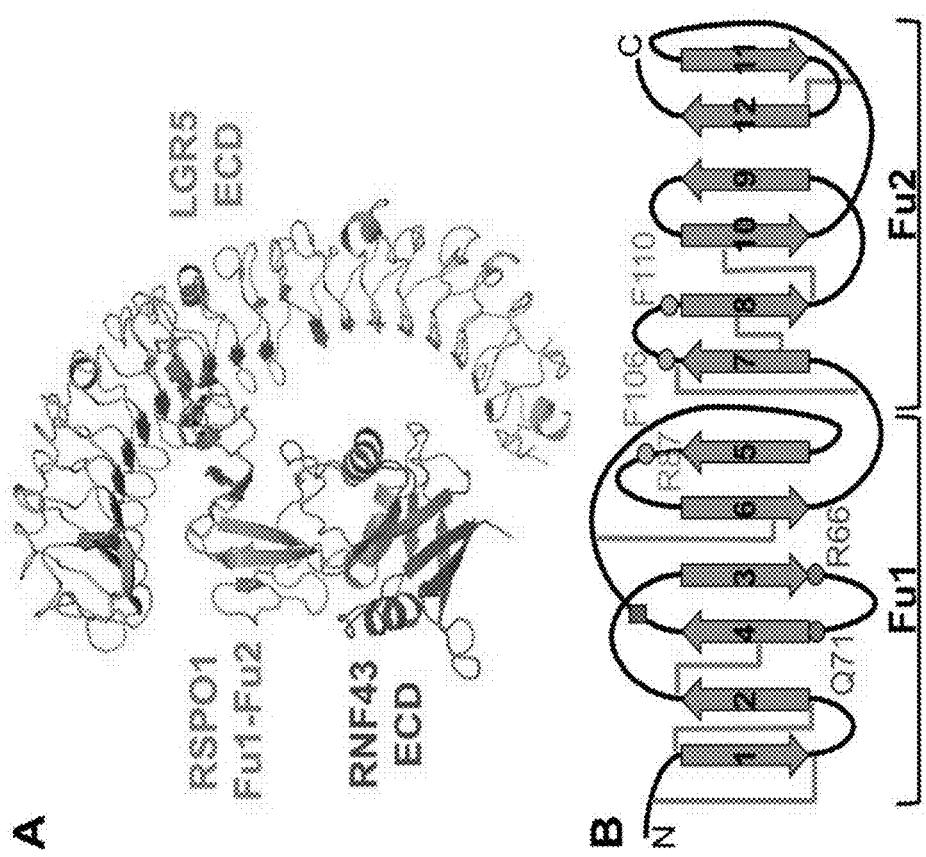

FIG. 4 shows the architecture of the ternary complex and chimera design. (A) Crystal structure of the ternary RSPO1 Fu1-Fu2:LGR5 ECD:RNF43 ECD complex. PDB ID: 4KNG. (B) Topology of the RSPO Fu1-Fu2 module highlighting ZNRF3/RNF43 and LGR4/5/6 interacting regions and chimera fusion point. Disulfide bonds are shown as brown connecting lines, cyan circles show conserved RSPO residues critical for interaction with LGR4/5/6, magenta circles highlight conserved RSPO residues critical for interaction with ZNRF3/RNF43, and the red square indicates the chimera junction point. Residue numbers correspond to RSPO1.

Figure 2:
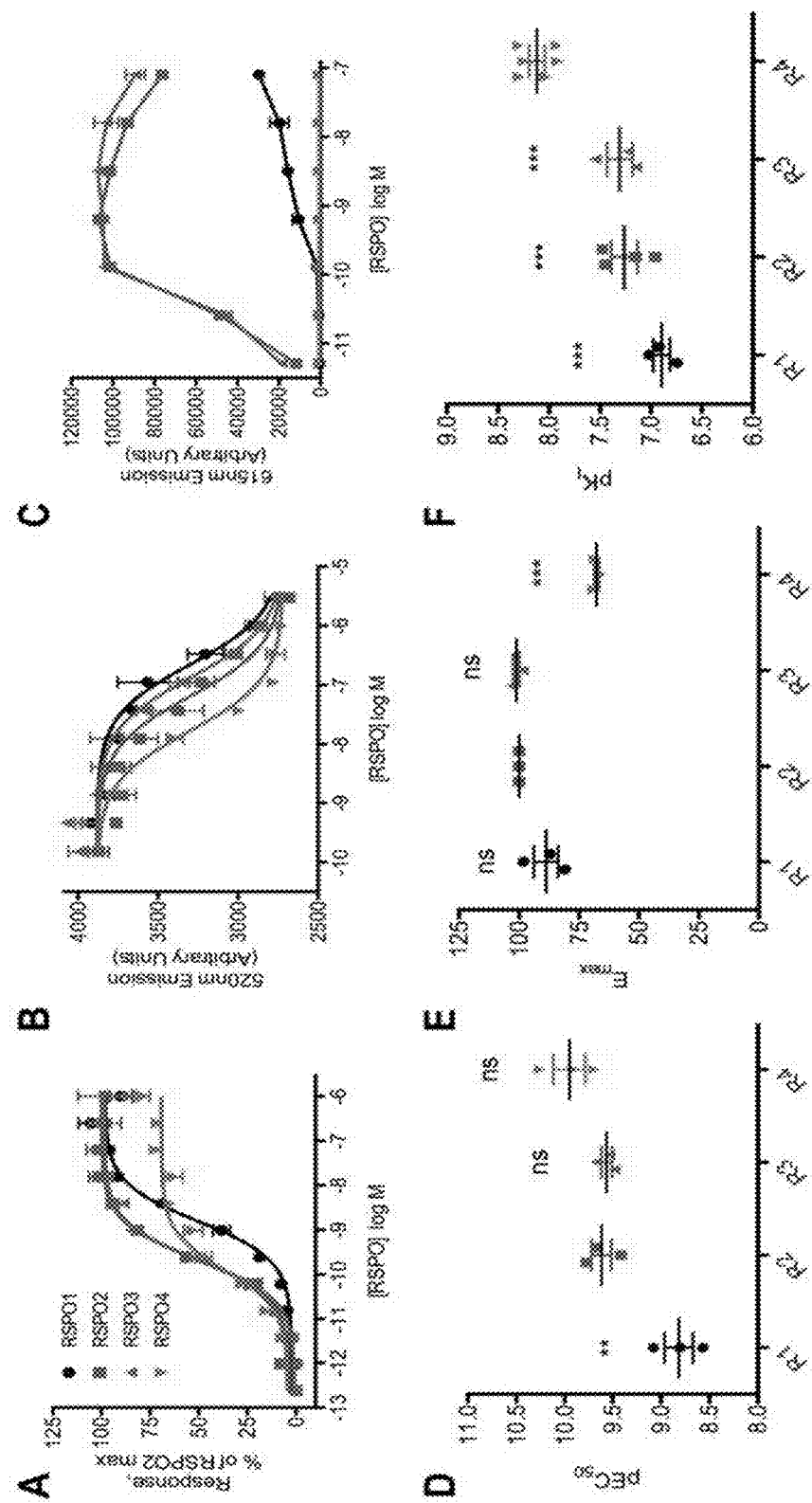
FIG. 2 shows the signaling and receptor binding activities of bacterially produced recombinant MBP-Th-RSPO1-4 Fu1-Fu2 proteins. (A) Potentiation of Wnt3a activation of the canonical Wnt/β-catenin pathway. HEK293T cells transfected with TOPFLASH firefly luciferase reporter and Renilla luciferase control plasmids were treated with the indicated concentrations of MBP-Th-RSPO Fu1-Fu2 proteins in 1:6 diluted Wnt3a conditioned media. (B) Binding of MBP-Th-RSPO1-4 Fu1-Fu2 proteins to the LGR4 ECD in vitro by TR-FRET competition assay. Tb-chelate-labeled MBP-Th-LGR4 LRR1-14 (20 nM) and AF488-labeled MBP-Th-RSPO2 Fu1-Fu2 (125 nM) were incubated with the indicated concentrations of unlabeled MBP-Th-RSPO Fu1-Fu2 proteins. (C) AlphaLISA® luminescent proximity assay (BMG Labtech GmbH, Ortenberg, Germany) for ZNRF3 ECD binding. The indicated concentrations of MBP—Th-RSPO Fu1-Fu2 proteins were incubated with 3 nM Biotin-ZNRF3 ECD. Donor and acceptor beads were at 20 µg/ml each. Data shown for panels A-C are representative of at least three independent experiments, each performed in duplicate. The error bars represent the S.E.M. of the experiment. (D, E, F) Vertical scatter plots showing the pECso, $E_{max}$, and $pK_1$ values obtained from replicate independent signaling and LGR4 binding experiments as in panels A and B. The mean values and error bars representing the S.E.M. of the replicates are denoted. Statistical significance from one-way ANOVA with Tukey's test is shown for comparison to RSPO2 in panels D and E and for comparison to RSPO4 in panel F.
Figure 5:
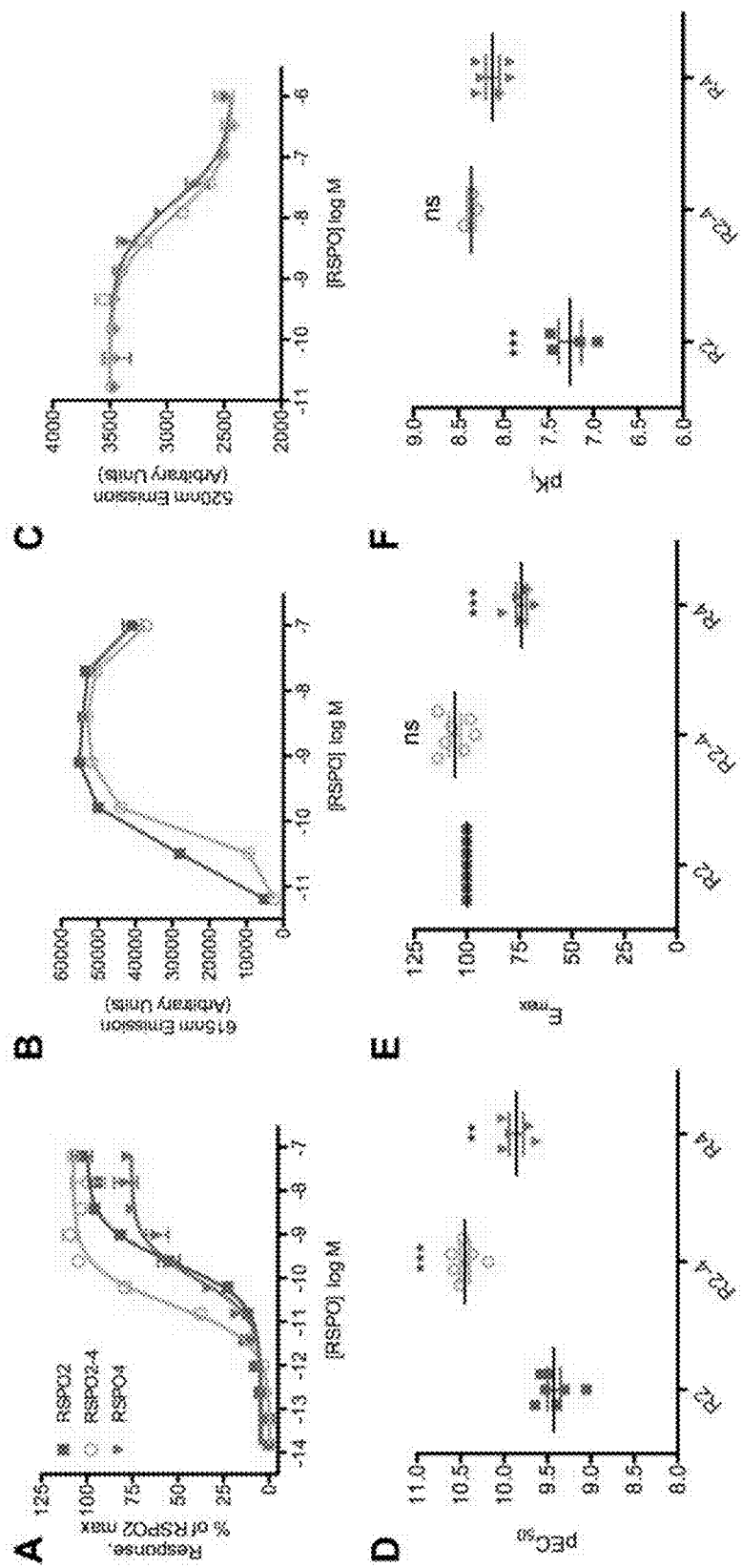

FIG. 5 illustrates the signaling and receptor binding activities of the RSPO2-4 chimera. (A) TOPFLASH Wnt signaling assay with the indicated MBP-Th-RSPO Fu1-Fu2 proteins. Data shown are representative of at least five experiments, each performed in duplicate. The error bars represent the S.E.M. of the experiment. (B) ZNRF3 binding AlphaLISA® assay (BMG Labtech GmbH, Ortenberg, Germany) as in FIG. 2(C) except that donor and acceptor beads were at 15 μg/ml each. Data shown are representative of three independent experiments, each performed in duplicate. The error bars represent the S.E.M. of the experiment. (C) LGR4 binding TR-FRET competition assay as in FIG. 2(B). Data shown are representative of at least three independent experiments, each performed in duplicate and the error bars represent S.E.M. of the experiment. (D, E, F) Vertical scatter plots showing the $pEC_{50}$, $E_{max}$, and $pK_1$ values obtained from replicate independent signaling and LGR4 binding experiments as in panels A and C. The mean values and error bars representing the S.E.M. of the replicates are denoted. Statistical significance from one-way ANOVA with Tukey's test is shown for comparison to RSPO2 in panels D and E and for comparison to RSPO4 in panel F.

Figure 6:
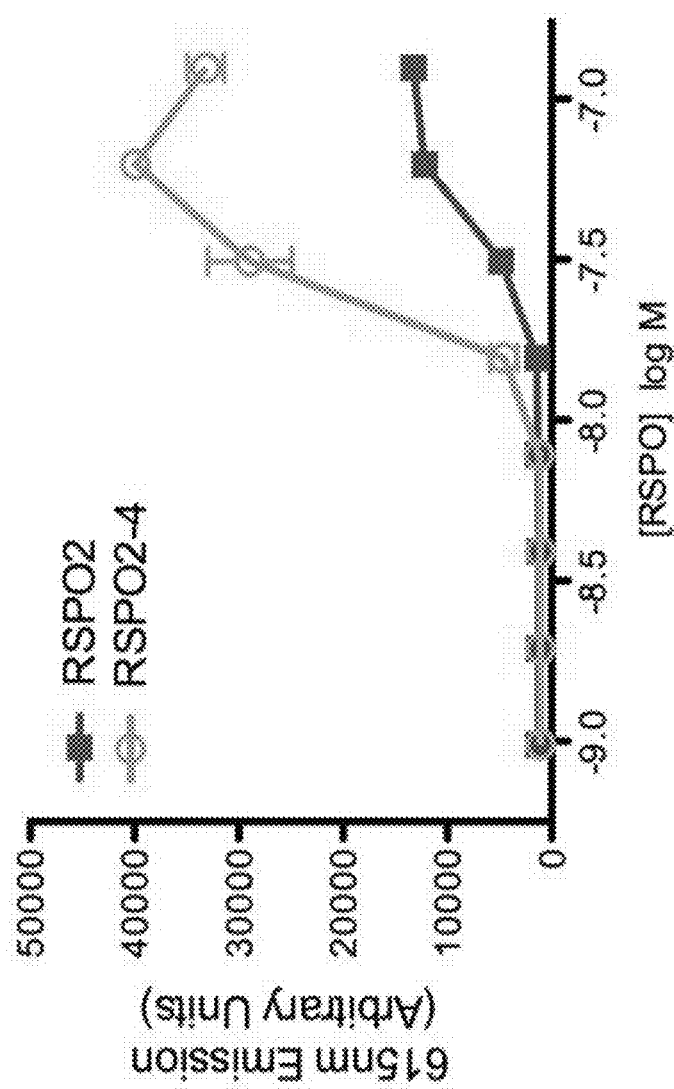

FIG. 6 shows an AlphaLISA® assay (BMG Labtech GmbH, Ortenberg, Germany) for ternary complex formation. The indicated concentrations of bacterially produced MBP-free RSPO2 and 2-4 chimera Fu1-Fu2 proteins were incubated with 5 nM Biotin-ZNRF3 ECD, 5 nM MBP-Th-LGR4 LRR1-14, and 15 μg/ml each donor and acceptor beads. Data shown are representative of two independent experiments, each performed in duplicate. The error bars represent the S.E.M. of the experiment.

Figure 7:
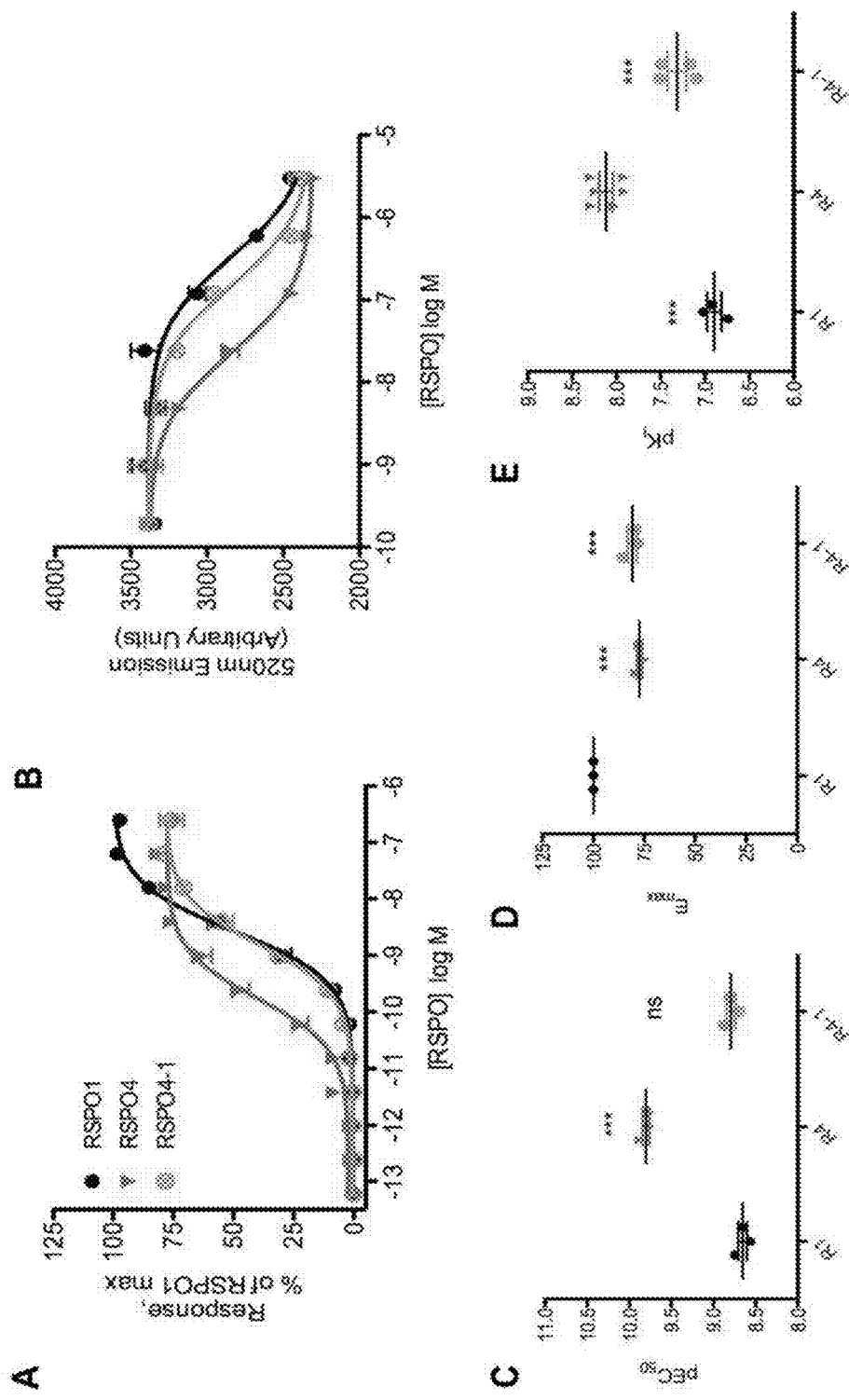

FIG. 7 shows the signaling and LGR4 binding activities of the RSPO4-1 chimera. (A) TOPFLASH Wnt signaling assay with the indicated MBP-Th-RSPO Fu1-Fu2 proteins. Data shown are representative of three independent experiments, each performed in duplicate. The error bars represent the S.E.M. of the experiment. (B) LGR4 binding TR-FRET competition assay as in FIG. 2(B). Data shown are representative of at least three independent experiments, each performed in duplicate. The error bars represent the S.E.M. of the experiment. (C, D, E) Vertical scatter plots showing the $pEC_5$, $E_{max}$, and $pK_I$ values obtained from replicate independent signaling and LGR4 binding experiments as in panels A and B. The mean values and error bars representing the S.E.M. of the replicates are denoted. Statistical significance from one-way ANOVA with Tukey's test is shown for comparison to RSPO1 in panels C and D and for comparison to RSPO4 in panel E.

Figure 8:
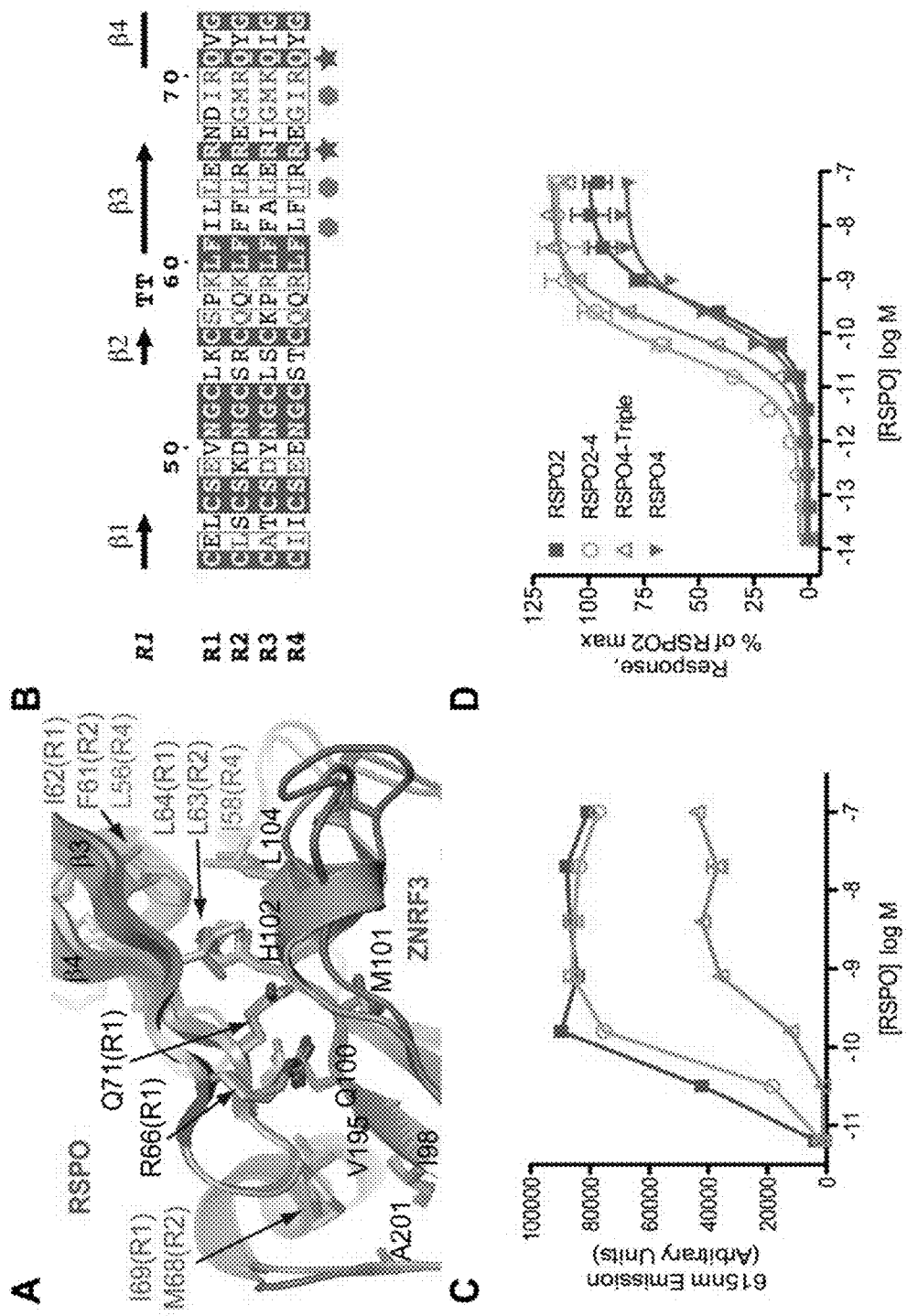

FIG. 8 illustrates the increasing RSPO4 signaling potency and efficacy with amino acid substitutions that increase affinity for ZNRF3. (A) Superimposed crystal structures of RSPO1 and -2 Fu1-Fu2 bound to ZNRF3 ECD highlighting conserved and non-conserved interactions involving the $2^{nd}$ RSPO β-hairpin. RSPO1 and RSPO2 are dark and light green, respectively, and the ZNRF3 ECDs are shown in shades of magenta. Modeled RSPO4 residues L56 and I58 are shown in orange. PDB ID: 4C9R and 4CDK. (B) Amino acid sequence alignment of the four human RSPOs for the ZNRF3/RNF43-interacting region. R1 is amino acids 44-73 of SEQ ID NO:1; R2 is amino acids 43-72 of SEQ ID NO:2; R3 is amino acids 45-74 of SEQ ID NO:3; and R4 is amino acids 38-67 of SEQ ID NO:4. Conserved RSPO residues involved in ZNRF3/RNF43 interaction are highlighted with green stars, and the variable positions in β-strand 3 that contact ZNRF3/RNF43 are highlighted with orange hexagons. (C) ZNRF3 binding AlphaLISA® assay (BMG Labtech GmbH, Ortenberg, Germany) performed as in FIG. 2(C), except that donor and acceptor beads were at 15 μg/ml each. Data shown are representative of at least two independent experiments, each performed in duplicate. The error bars represent the S.E.M. of the experiment. (D) TOPFLASH Wnt signaling assay with the indicated MBP-Th-RSPO Fu1-Fu2 proteins. Data shown are representative of at least four independent experiments, each performed in duplicate. The error bars represent the S.E.M. of the experiment.

FIG. 9 shows SEQ ID NO:9, which represents the amino acid sequence of an R-spondin Fu1-Fu2 chimera; amino acids 1-55 comprise amino acids 22-76 of RSPO2 (a ZNRF3 binding region), and amino acids 56-122 comprise amino acids 72-138 of RSPO4 (an LGR4 binding region). The boldfaced residues (at positions 56, 59, 62, 64, 66-69, and 73-74) indicate residues of RSPO4 Fu1 which differ from corresponding residues of RSPO2 Fu1. The corresponding RSPO2 Fu1 residues (i.e., amino acids 77-95 of SEQ ID NO:2) are indicated in boldface below the RSPO4 residues. The portion of Fu1 which comprises the beta 5 and beta 6 strands (contained within amino acids 56-74, indicated in italics) are derived from the Fu1 domain of RSPO4, rather than from the Fu1 domain of RSPO2 (the beta 5 and beta 6 strands are shown in FIG. 12).

FIG. 10 shows SEQ ID NO:10, which represents the amino acid sequence of an R-spondin Fu1-Fu2 chimera; amino acids 1-57 comprise amino acids 22-78 of RSPO3 (a ZNRF3 binding region), and amino acids 58-122 comprise amino acids 72-138 of RSPO4 (an LGR4 binding region). The boldfaced residues (at positions 58, 61, 64, 66, 68-71, and 75) indicate residues of RSPO4 Fu1 which differ from corresponding residues of RSPO3 Fu1. The corresponding RSPO3 Fu1 residues (i.e., amino acids 79-96 of SEQ ID NO:3) are indicated in boldface below the RSPO4 residues. The portion of Fu1 which comprises the beta 5 and beta 6 strands (contained within amino acids 58-76, indicated in italics) are derived from the Fu1 domain of RSPO4, rather than from the Fu1 domain of RSPO3 (the beta 5 and beta 6 strands are shown in FIG. 12).

Figure 11:
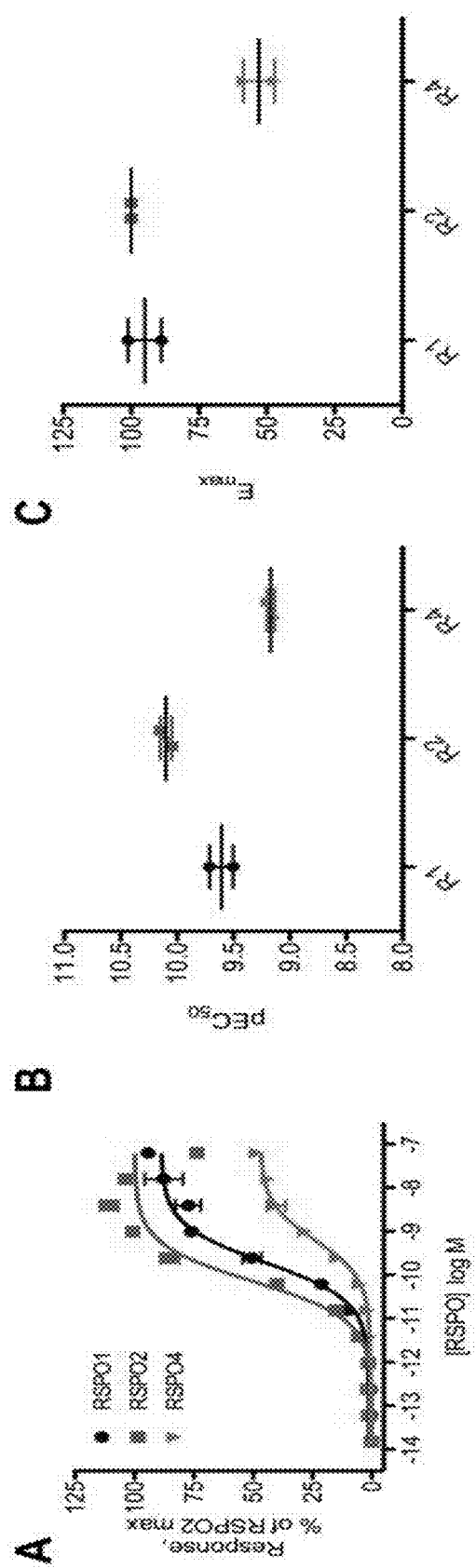

FIG. 11 confirms the signaling activities of commercially available recombinant RSPO proteins. (A) TOPFLASH Wnt signaling assay for RSPO1, RSPO2, and RSPO4 proteins purchased from R&D Systems, Inc. (Minneapolis, Minn.). Data shown are representative of two independent experiments, each performed in duplicate. The error bars represent the S.E.M. of the experiment. (B and C) Vertical scatter plots showing the $pEC_{50}$ and $E_{max}$ values obtained from two independent experiments as in panel A. The mean values and error bars representing the S.E.M. of the replicates are denoted.

Figure 12:
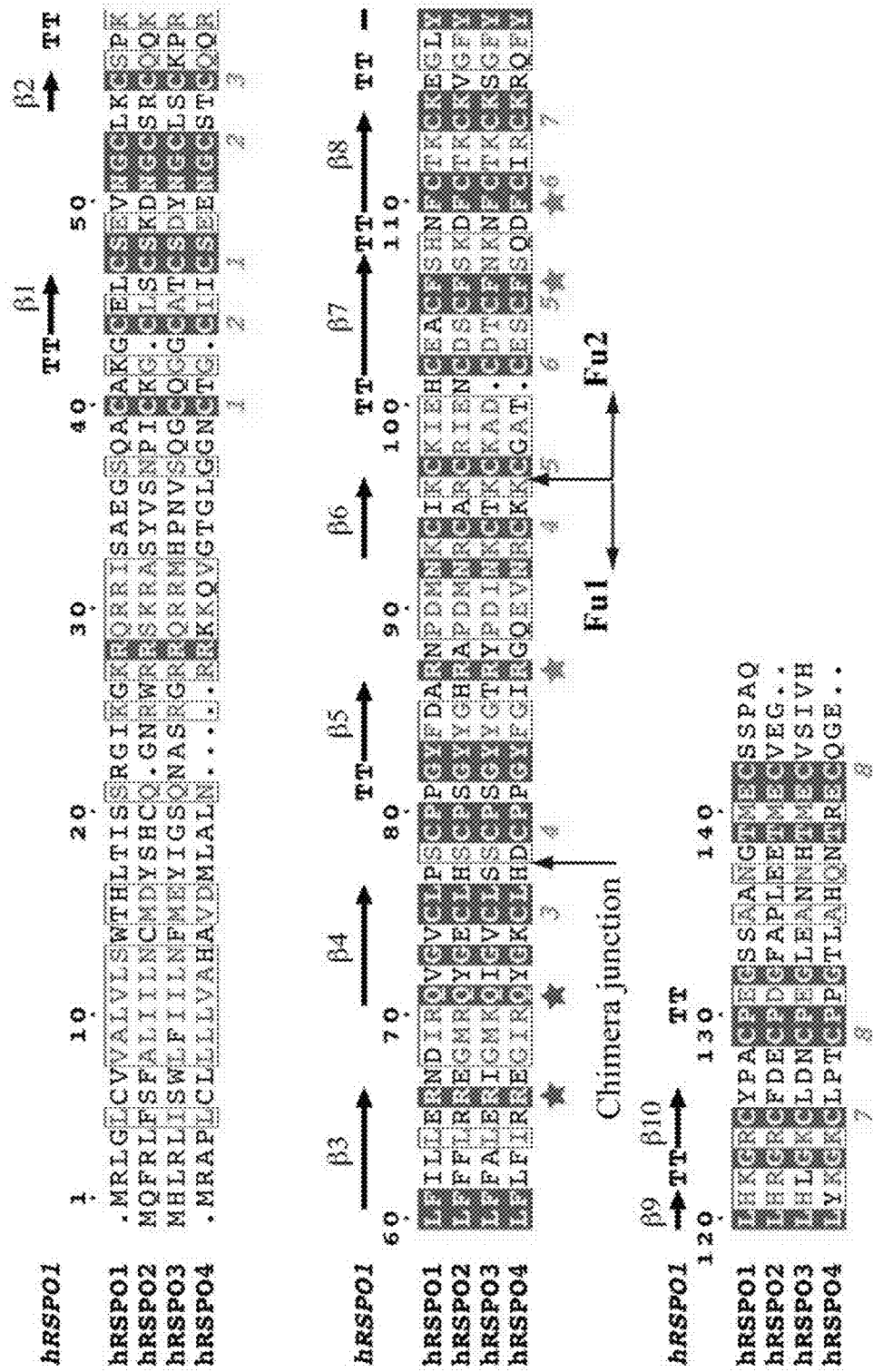

FIG. 12 shows an amino acid sequence alignment of the four human RSPOs for the signal peptide-Fu1-Fu2 regions. hRSPO1 is SEQ ID NO:1; hRSPO2 is SEQ ID NO:2; hRSPO3 is SEQ ID NO:3; and hRSPO4 is SEQ ID NO:4. Numbering at the top corresponds to hRSPO1. Disulfide bond connectivity is denoted with green numbers at the bottom. Magenta stars highlight conserved residues critical for ZNRF3/RNF43 interaction, and cyan stars highlight conserved residues critical for LGR4/5/6 interaction.

Figure 13:
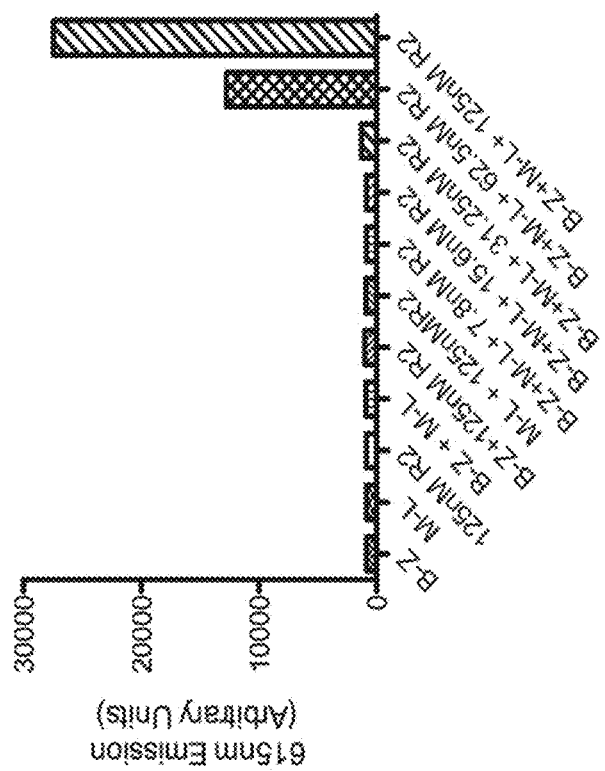

FIG. 13 shows an AlphaLISA® ternary complex control assay (BMG Labtech GmbH, Ortenberg, Germany). "B-Z" corresponds to 5 nM biotinylated ZNRF3; "M-L" corresponds to 5 nM MBP-LGR4; and "R2" is MBP free RSPO2 in different [nM] amounts. All contain 15 µg/ml each of streptavidin and anti-MBP beads.

Figure 14:
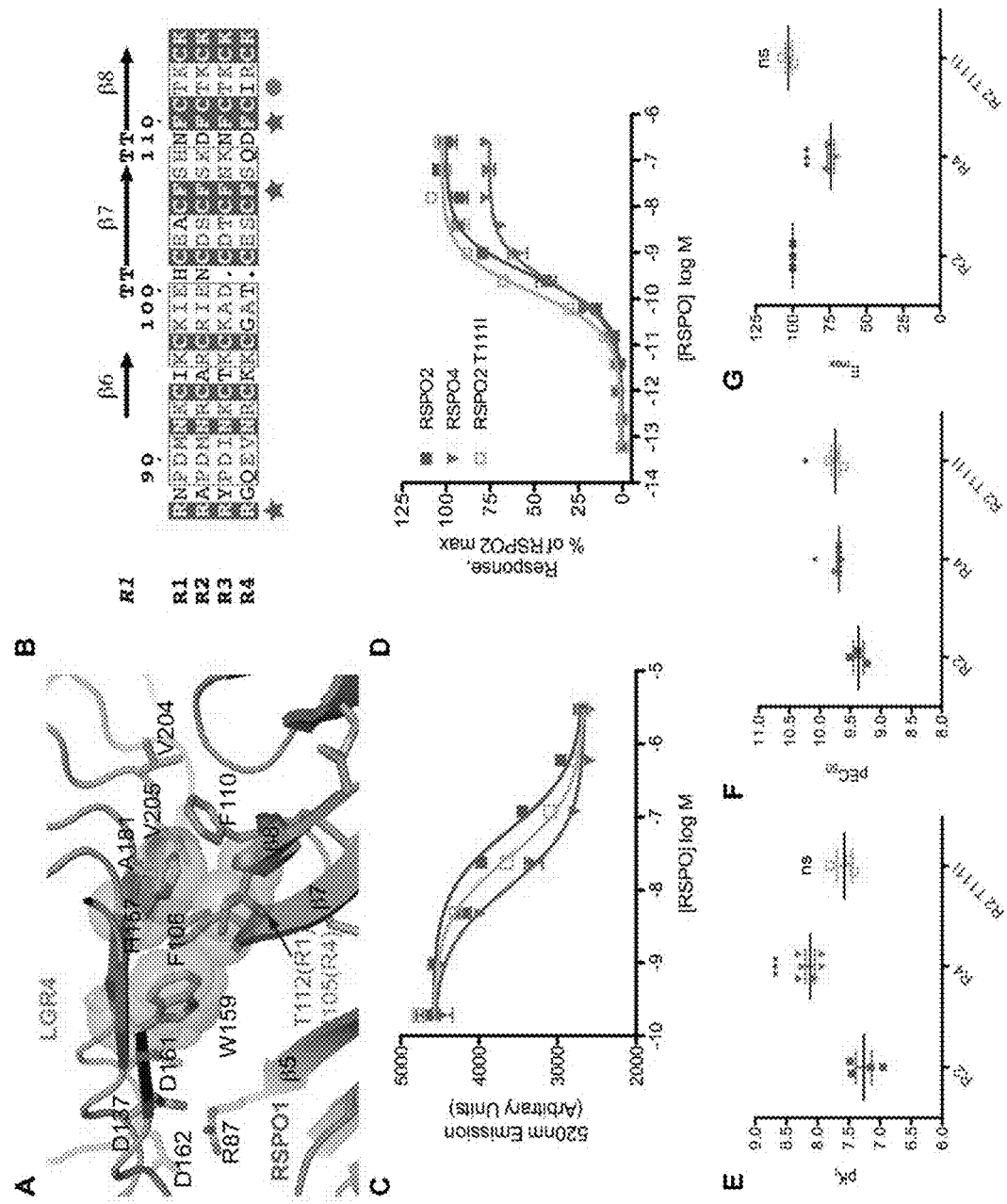

FIG. 14 shows an embodiment for increasing RSPO2 signaling potency with an amino acid substitution that increases affinity for LGR4. (A) Crystal structure of RSPO1 Fu1-Fu2 bound to LGR4 ECD highlighting conserved interactions and the non-conserved position 112. T112 is overlaid with a modeled isoleucine (I105 in RSPO4). Space-filling spheres are shown for LGR4 W159, H157, and the modeled isoleucine at RSPO1 position 112. PDB ID: 4KT1. (B) Amino acid sequence alignment of the four human RSPOs for the LGR4/5/6-interacting region. R1 is amino acids 87-115 of SEQ ID NO:1; R2 is amino acids 86-114 of SEQ ID NO:2; R3 is amino acids 88-115 of SEQ ID NO:3; and R4 is amino acids 81-108 of SEQ ID NO:4. Conserved RSPO residues involved in LGR4/5/6 interaction are highlighted with green stars, and the variable Thr/Ile at position 112 (RSPO1 numbering) is highlighted with an orange hexagon. (C) LGR4 binding TR-FRET competition assay as in FIG. 2(B). Data shown are representative of at least three independent experiments, each performed in duplicate. The error bars represent the S.E.M. of the experiment. (D) TOPFLASH Wnt signaling assay with the indicated MBP-Th-RSPO Fu1-Fu2 proteins. (E, F, G) Vertical scatter plots showing the pK, pECso, and $E_{max}$ values obtained from replicate independent LGR4 binding and signaling experiments as in panels C and D. The mean values and error bars representing the S.E.M. of the replicates are denoted. Statistical significance from one-way ANOVA with Tukey's test is shown for comparison to RSPO2 in panels E-G.

Figure 15A:
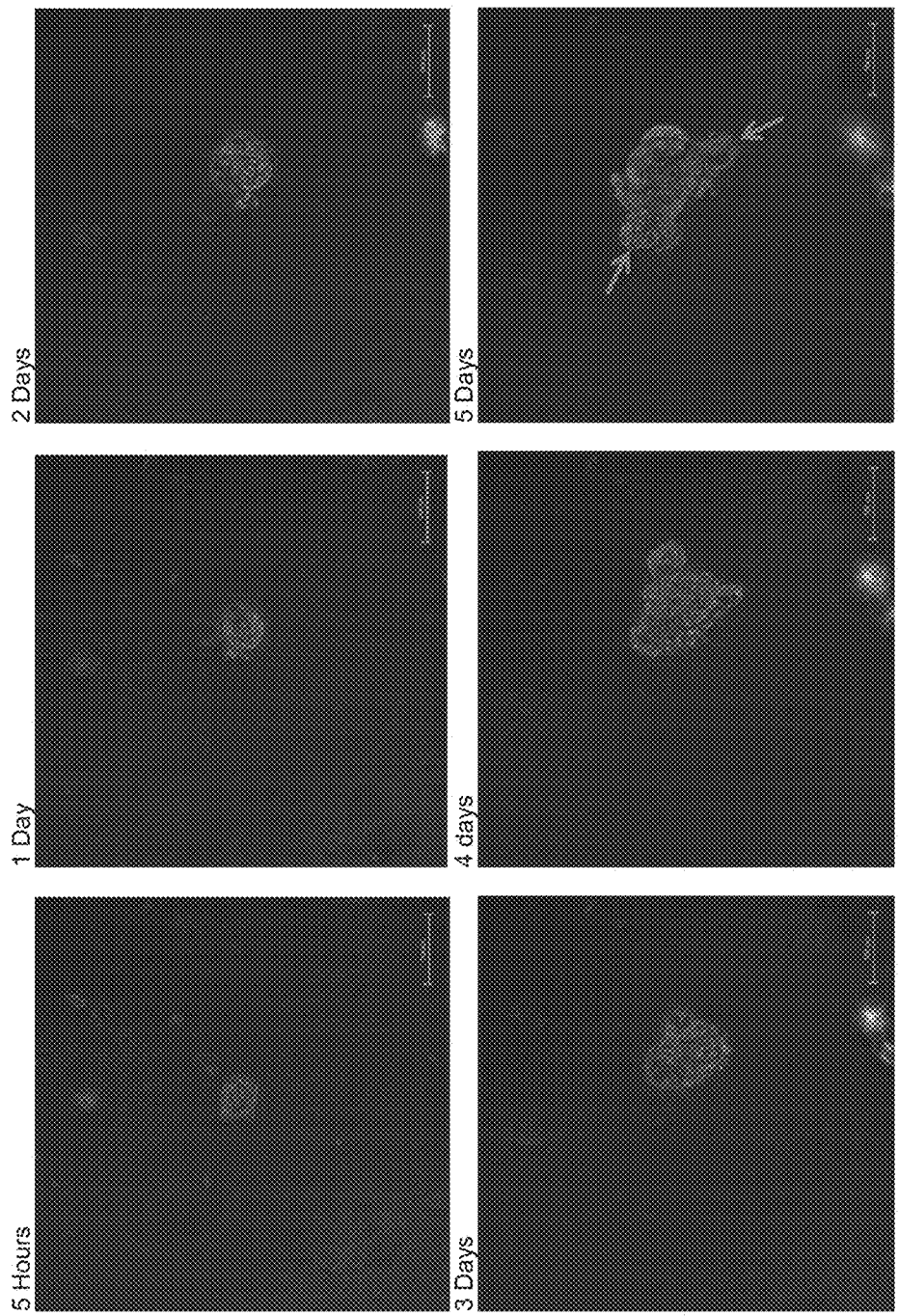

FIG. 15A shows primary mouse intestinal organoid culture imaged by brightfield microscopy over 5 days. A single isolated intestinal crypt growing into an organoid in the presence of 2 nM RSPO2-4 Fu1-Fu2-$H_6$ (RSPO2-4 variant) (produced in E. coli) was observed. Arrows indicate budding crypt structures. The scale bars represent 100 µm.

Figure 15B:
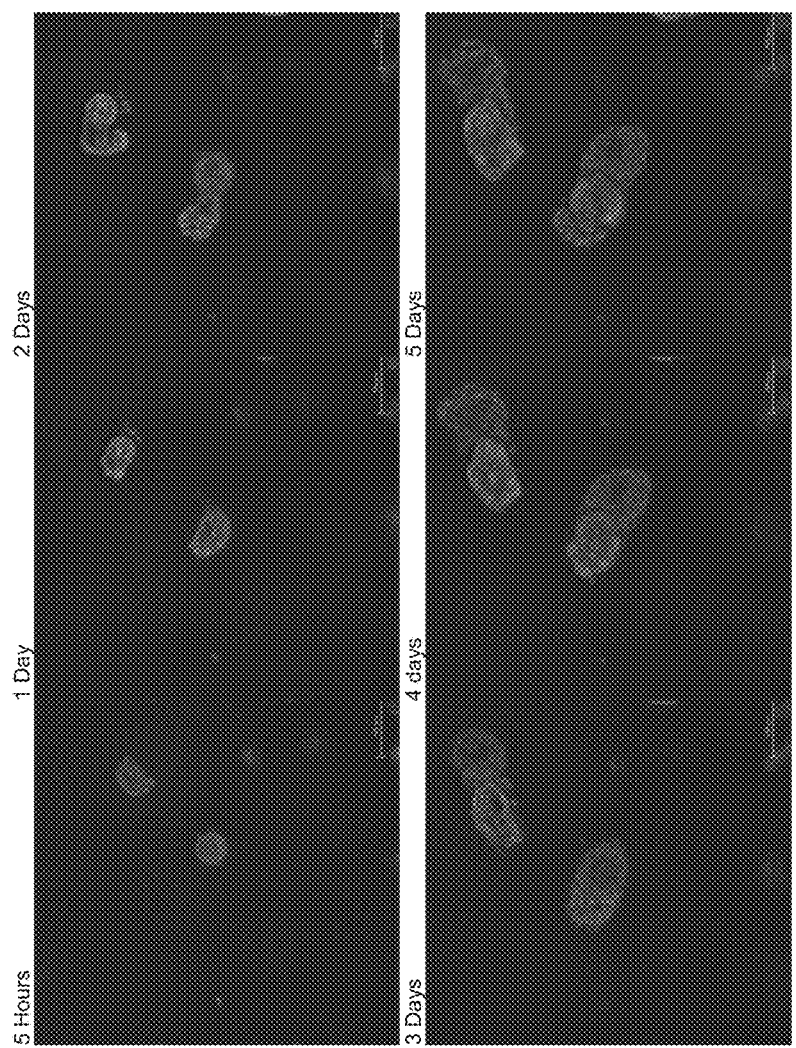

FIG. 15B shows two isolated intestinal crypts growing into organoids in the presence of 2 nM RSPO2 Fu1-Fu2-$H_6$ (produced in E. coli) over 5 days. The scale bars represent 100 µm.

Figure 16:
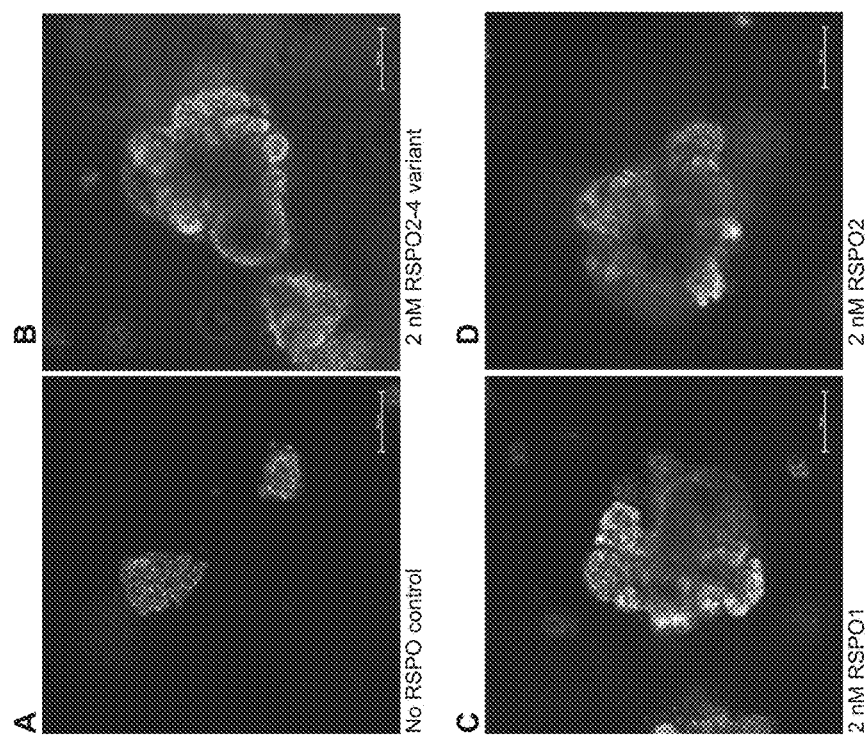

FIG. 16 shows primary mouse intestinal organoid culture visualized by brightfield microscopy after 11 days in culture and one media change. Images show organoids cultured in the presence of the indicated E. coli-produced RSPO Fu1-Fu2-$H_6$ proteins at 2 nM. (A) Control—No RSPO, (B) RSPO2-4 variant, (C) RSPO1, (D) RSPO2. Scale bars represent 100 µm.

Figure 17:
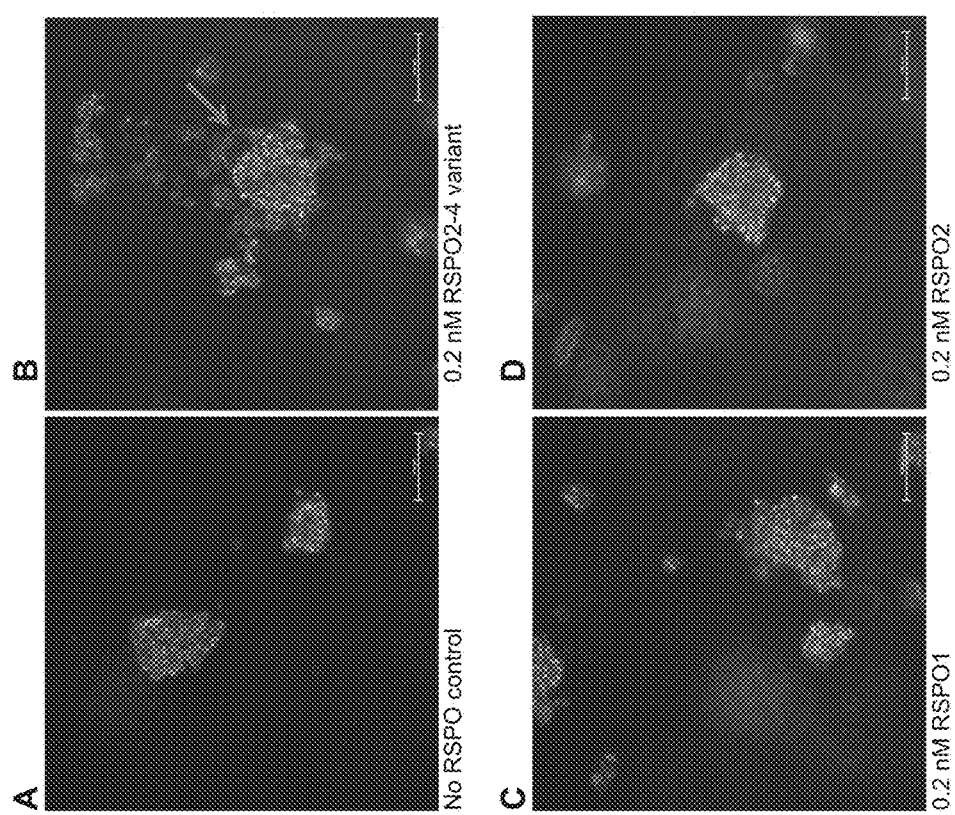

FIG. 17 shows primary mouse intestinal organoid culture visualized by brightfield microscopy after 11 days in culture and one media change. Images show organoids cultured in the presence of the indicated E. coli-produced RSPO Fu1-Fu2-$H_6$ proteins at 0.2 nM. (A) Control—No RSPO, (B) RSPO2-4 variant, (C) RSPO1, (D) RSPO2. Scale bars represent 100 µm. The arrow indicates the beginnings of a budding structure.

Figure 18:
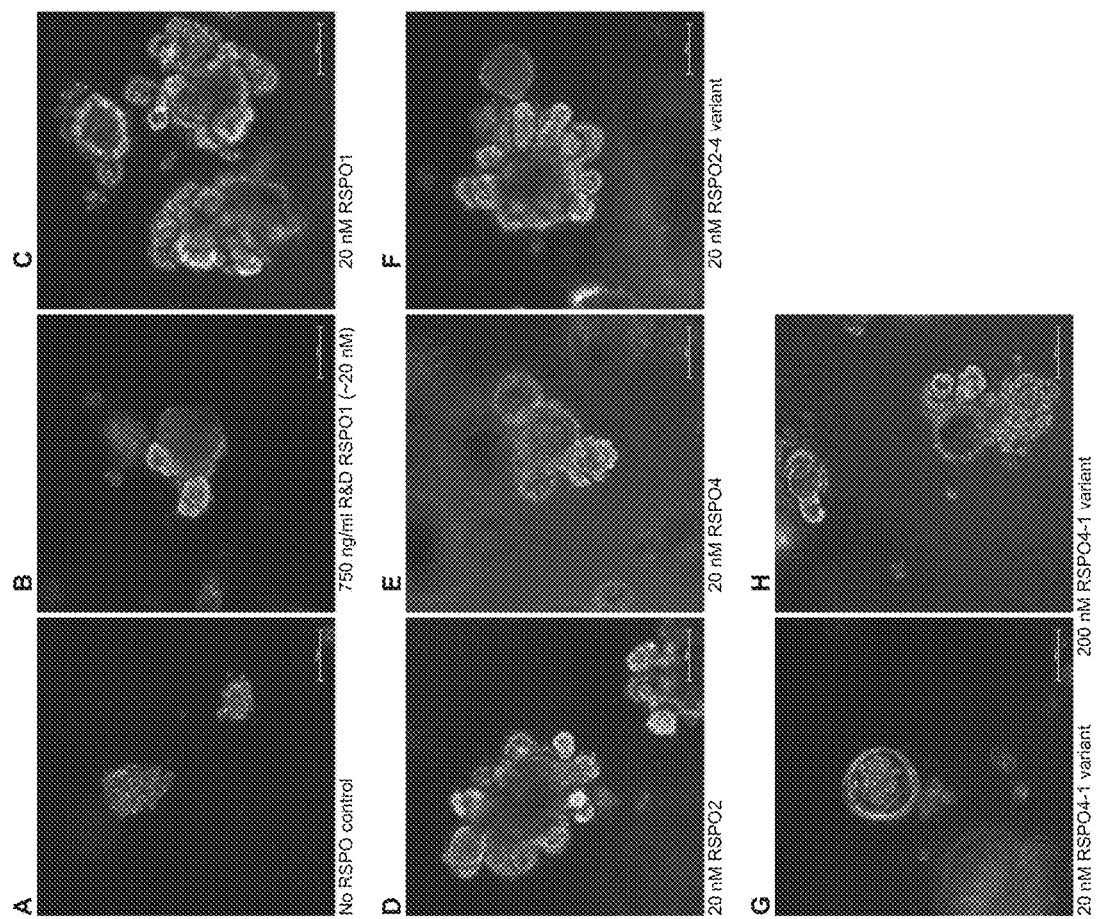

FIG. 18 shows primary mouse intestinal organoid culture visualized by brightfield microscopy after 11 days in culture and one media change. Images show organoids cultured in the absence (A-control) or presence of the indicated RSPO proteins at 20 nM (B-G) or 200 nM (H) as indicated. Scale bars represent 100 µm. Panel B shows organoid growth in the presence of full-length RSPO1 purchased from R&D Systems, Inc. (Minneapolis, Minn.); otherwise, all panels used RSPO Fu1-Fu2-$H_6$ proteins produced in E. coli.

DETAILED DESCRIPTION

Before further describing various embodiments of R-spondin variants, compositions, and methods of the present disclosure in more detail by way of exemplary description, examples, and results, it is to be understood that the present disclosure is not limited in application to the details of methods and compositions as set forth in the following description. The inventive concepts of the present disclosure are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the disclosure. All such similar substitutes and modifications apparent to those having ordinary skill in the art are deemed to be within the spirit, scope, and concept of the inventive concepts as described herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "variant" may be used interchangeably with the term "mutant" and "chimera" and refers to a protein, peptide, or nucleic acid which has at least one amino acid or nucleotide which is different from the wild type version of the protein, peptide or nucleic acid, and includes, but is not limited to, point substitutions, multiple contiguous or non-contiguous substitutions, chimeras, or fusion proteins, and the nucleic acids which encode them. RSPO2-4 refers to a chimera comprising portions of RSPO2 and RSPO4, and RSPO4-1 refers to a chimera comprising portions of RSPO1 and RSPO4.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic effect without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "homologous" or "% identity" as used herein means a nucleic acid (or fragment thereof) or a protein (or a fragment thereof) having a degree of homology to the corresponding natural reference nucleic acid or protein that may be in excess of 70%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in *Atlas of Protein Sequence and Structure*, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (*Proc. Natl. Acad. Sci. USA* (1990) 87:2264-2268, modified as in Karlin & Altschul, *Proc. Natl. Acad. Sci. USA* (1993) 90:5873-5877).

In one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same.

Another non-limiting example of a mathematical algorithm used for comparison of sequences is the algorithm of Myers & Miller (*CABIOS* (1988) 4:11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (*Proc. Natl. Acad. Sci. USA* (1988) 85:2444-2448).

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish ("Local alignment statistics," Doolittle ed., *Methods in Enzymology* (1996) 266:460-480); Altschul et al. (*Journal of Molecular Biology* (1990) 215:403-410); Gish & States (*Nature Genetics* (1993) 3:266-272); Karlin & Altschul (*Proc. Natl. Acad. Sci. USA* (1993) 90:5873-5877); all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information (Bethesda, Md.). These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a mutant R-spondin protein product (including, as noted above, chimeras and fusion proteins) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a mutant protein, or encoding a therapeutically-effective fragment of a mutant protein can be substantially the same as the coding sequence of the endogenous coding sequence as long as it encodes a biologically active mutant protein product. Further, the mutant protein, or therapeutically-effective fragment of a mutant protein may be expressed using polynucleotide sequence(s) which differ in codon usage due to the degeneracies of the genetic code or allelic variations. Moreover, the R-spondin mutants of the present disclosure and the nucleic acids which encode them include protein and nucleic acid variants which comprise additional conservative substitutions. For example, the R-spondin variants include, but are not limited to, variants that are not exactly the same as the sequences disclosed herein, but which have, in addition to the substitutions explicitly described for various sequences listed herein, conservative substitutions of amino acid residues which do substantially not impair the activity or properties of the variants described herein. Examples of such conservative amino acid substitutions include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

The terms "infection," "transduction," and "transfection" are used interchangeably herein and refer to introduction of a gene, nucleic acid, or polynucleotide sequence into cells such that the encoded protein product is expressed. The polynucleotides of the presently disclosed inventive concepts may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the presently disclosure. In light of the description in the present disclosure, one of ordinary skill in the art would readily know how to make, identify, select or test such variants for enhanced R-spondin activity. Further, one of ordinary skill in the art may optimize the expression of the R-spondin mutant polypeptides of the present disclosure to improve expression by any methods known in the art, including but not limited to, by removing cryptic splice sites, by adapting the codon usage by introducing a Kozak consensus sequence before the start codon, by changing the codon usage, or any combination thereof.

Abbreviations used herein include, for example: RSPO: R-spondin; Fu: Furin-like domain; LRR: leucine rich repeat; ECD: extracellular domain; MBP: maltose binding protein; Th: thrombin protease cleavage site; PEI: polyethyleneimine; BSA: bovine serum albumin; IPTG: isopropyl-β-D-thiogalactopyranoside; GSH: reduced glutathione; GSSG: oxidized glutathione; and SPR: surface plasmon resonance.

The present disclosure is based upon investigations in the molecular basis for the differing signaling strengths of the R-spondins RSPO1-RSPO4 using wild-type, mutant, and chimeric RSPO Fu1-Fu2, LGR4 ECD, and ZNRF3 ECD proteins in Wnt signaling and receptor binding assays. RSPO2, RSPO3, and RSPO4 were found to have similar signaling potencies that were each greater than that of RSPO1, whereas RSPO1, RSPO2, and RSPO3 had similar efficacies that were each greater than that of RSPO4. The RSPOs bound LGR4 with affinity rank order RSPO4>RSPO2 and RSPO3>RSPO1, and ZNRF3 with affinity rank order RSPO2 and RSPO3>>RSPO1>RSPO4. Eventually novel high-potency R-spondin variants were obtained. In one embodiment, a novel R-spondin chimera, designated herein as "RSPO2-4 chimera" or "RSPO2-4 variant" (combining an RSPO2 ZNRF3 binding region with an RSPO4 LGR4 binding region) exhibited enhanced ternary complex formation and 10-fold stronger signaling potency than RSPO2 and had efficacy equivalent to RSPO2. Point substitution mutations conferring increased ZNRF3 binding upon RSPO4 or increased LGR4 binding upon RSPO2 enhanced signaling potency of the mutants. The results indicate that signaling potency of R-spondins is determined by the ability of the R-spondin to form a ternary complex, while efficacy depends on ZNRF3 recruitment.

Certain non-limiting embodiments of the present disclosure are directed to R-spondin variants that include at least two regions: a ZNRF3 binding region of a first R-spondin and an LGR4 binding region of a second R-spondin. These R-spondin variants have ZNRF3 and LGR4 binding activity. Any R-spondin ZNRF3 and LGR4 binding regions known in the art or otherwise contemplated herein, or variants/mutants of said binding regions that retain the associated binding activity, may be utilized in accordance with the present disclosure. In a particular non-limiting embodiment, the first R-spondin is R-spondin-2 or R-spondin-3, and the second R-spondin is R-spondin-4. In another particular non-limiting embodiment, the ZNRF3 binding region comprises an amino acid sequence having at least 90% identity to amino acids 22-76 of SEQ ID NO:2 or to amino acids 22-78 of SEQ ID NO:3, and the LGR4 binding region comprises an amino acid sequence having at least 90% identity to amino acids 72-138 of SEQ ID NO:4. In yet another particular non-limiting embodiment, the R-spondin variant includes: (a) an amino acid sequence having at least 90% identity to amino acids 22-144 of SEQ ID NO:2 and comprising one or more substitutions thereto, wherein the amino acid T in position 111 is substituted; and (b) an amino acid sequence having at least 90% identity to amino acids 21-138 of SEQ ID NO:4 and comprising one or more substitutions when compared to said sequence, wherein at least one of amino acids L, I, and I in positions 56, 58, and 63, respectively, is substituted. In a further non-limiting embodiment, the R-spondin variant includes: (a) or (b) an amino acid sequence having at least 90% identity to amino acids 22-146 of SEQ ID NO:3 and comprising one or more substitutions thereto, wherein the amino acid T in position 112 is substituted; and (b) an amino acid sequence having at least 90% identity to amino acids 21-138 of SEQ ID NO:4 and comprising one or more substitutions when compared to said sequence, wherein at least one of amino acids L, I, and I in positions 56, 58, and 63, respectively, is substituted.

Other non-limiting embodiments of the present disclosure are directed to a cell culture medium that includes any of the R-spondin variants described or otherwise contemplated herein.

Other non-limiting embodiments of the present disclosure are directed to a method of culturing cells responsive to an R-spondin. In the method, a quantity of said cells may be exposed to any of the R-spondin variants described or otherwise contemplated herein; alternatively, the quantity of said cells may be exposed to any of the cell culture medium containing at least one of any of the R-spondin variants described or otherwise contemplated herein. The cells are exposed under conditions suitable for growth of said cells; for example (but not by way of limitation), the conditions may be suitable for growing organoids of intestinal stem cells, colon cells, esophagus cells, small intestine cells, ovary cells, prostate cells, liver cells, or pancreas cells, or any cell type responsive to or requiring R-spondin protein.

Certain additional embodiments of the present disclosure are directed to a method of providing protection against chemotherapy-induced or radiation therapy-induced tissue damage in a subject in need of such therapy. In the method, an effective amount of at least one of any of the R-spondin variants described or otherwise contemplated herein is administered to the subject.

The present disclosure will be more readily understood by reference to the following examples and embodiments, which are included merely for purposes of illustration, and are not intended to be limiting. The following detailed examples and methods describe how to make and use the various mutant proteins of the present disclosure and are to be construed, as noted above, only as illustrative, and not as limitations of the disclosure in any way whatsoever. Those skilled in the art will promptly recognize appropriate variations from the materials and procedures described herein.

Materials and Methods

Plasmids and Plasmid Construction. Bacterial expression plasmids for wild-type human RSPO2, RSPO3, and RSPO4 Fu1-Fu2 proteins as maltose binding protein (MBP)-Thrombin cut site (Th)-RSPO Fu1-Fu2-$H_6$ fusions co-expressed with the bacterial disulfide bond isomerase DsbC were constructed with standard PCR and restriction endonuclease-based cloning techniques as described in Moad and Pioszak (Biochemistry (2013) 52(41):7295-7304). The bacterial expression plasmids for wild-type MBP-Th-hRSPO1 Fu1-Fu2-$H_6$ and MBP-Th-hLGR4.23-383-$H_6$ were previously described (Moad and Pioszak, 2013, op. cit.). A bacterial expression plasmid for in vivo site-specific biotinylation of the human ZNRF3 ECD was constructed by swapping the BamHI-NotI ECD-encoding fragment from pAP353 (Moad and Pioszak, 2013, op. cit.) into a plasmid previously described plasmid in Pioszak et al. (*J Biol Chem* (2009) 284(41):28382-28391) to enable co-expression of an MBP-Th-Avi tag-ZNRF3 ECD-$H_6$ fusion with the BirA biotin ligase. Chimeric RSPO and RSPO point mutant bacterial expression plasmids were constructed using either the Gibson Assembly cloning method with Gibson Assembly Master Mix (New England Biolabs, Ipswich, Mass.) or the QuikChange II site directed mutagenesis kit (Agilent Technologies, Santa Clara, Calif.). A plasmid for expression of MBP-Th-hRSPO4 Fu1-Fu2-$H_6$ secreted from HEK293T cells was constructed by PCR amplifying the fusion protein-encoding fragment from the corresponding bacterial expression plasmid as an AgeI-KpnI fragment and ligating into plasmid pHLSec ("A time- and cost-efficient system for high-level protein production in mammalian cells." *Acta crystallographica Section D, Biological crystallography* 62(Pt 10): 1243-1250). Primer sequences are available from the authors upon request. The following plasmids were constructed for this work (amino acid residue numbers are indicated): pAC018, pETDuet1/MBP-Th-RSPO2.22-144-$H_6$/DsbC; pAP355, pETDuet1/MBP-Th-RSPO3.22-146-$H_6$/DsbC; pAP356, pETDuet1/MBP-Th-RSPO4.21-138-$H_6$/DsbC; pMW012, pETDuet1/MBP-Th-RSPO4.21-138-$H_6$ (L56F, I58L, 163M)/DsbC; pMW015, pETDuet1/MBP-Th-RSPO2.22-76-RSPO4.72-138-$H_6$/DsbC [2-4 chimera]; pMW018, pETDuet1/MBP-Th-RSPO4.21-71-RSPO1.78-145-$H_6$/DsbC [4-1 chimera]; pMW017, pETDuet1/MBP-Th-Avi tag-ZNRF3.56-216-$H_6$/BirA; pTB025, pHLSec/MBP-Th-RSPO4.21-138-$H_6$; pTB032, pETDuet1/MBP-Th-RSPO2.22-144-$H_6$ (T111I)/DsbC.

Protein Expression and Purification. MBP-Th-RSPO Fu1-Fu2 and MBP-Th-LGR4 LRR1-14 proteins were expressed in *E. coli* Origami B (DE3) cells as described in Hill and Pioszak (*Protein expression and purification* (2013) 88(1): 107-113), and Moad and Pioszak (2013, op. cit.). To facilitate in vivo biotinylation of MBP-Th-Avi tag-ZNRF3 ECD, Origami B (DE3) cells were co-transformed with plasmids pMW017 and pACYCDuet1/DsbC (Pioszak et al., 2009, op. cit.). Expression was carried out as for the other proteins except that the growth media included ampicillin and chloramphenicol and 50 μM Biotin was added to the media upon induction with IPTG. The MBP-Th-RSPO Fu1-Fu2 and MBP-Th-LGR4 LRR1-14 fusion proteins were purified as previously described (Moad and Pioszak, 2013, op. cit.), except that 0.5-1 mM EDTA was included in the buffers for amylose, gel-filtration, and ion exchange chromatography and all buffers were degassed before use. The redox buffer conditions used for the RSPO2-4 chimera and RSPO4-1 chimera were 1 mM GSH/1 mM GSSG and 5 mM GSH/1 mM GSSG, respectively.

MBP-Th-biotin-ZNRF3 ECD-$H_6$ was purified as previously described for non-biotinylated ZNRF3 ECD through the gel-filtration step (Moad and Pioszak, 2013, op. cit.). The peak gel-filtration fractions were pooled and digested with human α-thrombin protease (HTI) at a 1:300 (thrombin weight: protein weight) ratio at 4° C. overnight in gel filtration buffer. The digested sample was loaded onto a 5 mL monomeric avidin column (Thermo/Pierce) previously washed in 25 mL of binding buffer (50 mM Tris-HCl (pH 7.5), 10% (v/v) glycerol, 150 mM NaCl, and 0.5 mM EDTA); 15 mL of elution buffer (50 mM Tris-HCl (pH7.5), 5% (v/v) glycerol, 150 mM NaCl, and 2 mM Biotin); 25 mL of regeneration buffer (0.1 M glycine pH 2.8); and 25 mL of binding buffer. The column was washed with 200 mL of binding buffer and eluted with 25 mL of elution buffer. The eluted protein was concentrated using a 9 kDa molecular weight cutoff spin concentrator (Thermo Fisher Scientific, Inc., Rockford, Ill.) and subjected to a final gel-filtration chromatography step as above.

RSPO Fu1-Fu2 proteins free of MBP were prepared by digesting their respective fusion proteins with human α-thrombin protease at a 1:300 ratio overnight at 4° C. with dialysis to 50 mM Na/K phosphate (pH 7.0) and 5% (v/v) glycerol (S buffer A). The digested sample was applied to a 5 mL SPFF cation exchange column (GE Healthcare Bio-Sciences, Pittsburgh, Pa.), washed in S buffer A, then eluted with a linear gradient of 0 to 1 M NaCl in S buffer A. Peak fractions were concentrated and subjected to a final gel-filtration step as above.

MBP-Th-RSPO4 Fu1-Fu2-$H_6$ was expressed as a secreted glycoprotein from HEK293T cells using PEI-mediated transient transfection with plasmid pTB025 according to standard methods (Aricescu et al., 2006, op. cit.). The fusion protein was purified from the media on a 5 mL prepacked Ni-chelating Sepharose column (GE Healthcare Bio-Sciences, Pittsburgh, Pa.) followed by gel-filtration chromatography performed as for the other proteins.

All purified proteins were dialyzed to storage buffer containing 25 mM HEPES (pH 7.5), 50% (v/v) glycerol, and 150 mM NaCl for long-term storage at −80° C. Protein concentrations were determined by the Bradford method with a BSA standard curve and are stated in terms of the monomers. In some cases protein concentrations were verified by UV absorbance at 280 nm. Commercial recombinant RSPO1, RSPO2, and RSPO4 were from R&D Systems, Inc. (Minneapolis, Minn.; catalog numbers 4645-RS-025/CF, 3266-RS-025/CF, and 4575-RS-025/CF) and they were reconstituted according to the manufacturer's directions. In place of the $H_6$ tags (SEQ ID NO:30) attached to the recombinant proteins described herein for enhanced purification, other purification-enhancing tags could be used. The identity of the specific tag to be used is not critical as long as the tag is capable of being expressed with the recombinant protein and is capable of being immobilized on a suitable surface or carrier material. A number of suitable tags which are known and/or commercially available and may be used, include, but are not limited to, SEQ ID NOS:30-36.

LanthaScreen® TR-FRET Assay (Thermo Fisher Scientific Inc., Rockford, Il.) for LGR4 ECD Binding. Labeling of proteins with donor and acceptor fluorophores was performed as previously described (Moad and Pioszak, 2013, op. cit.) with the following alterations. MBP-Th-LGR4 was labeled with amine reactive Terbium chelate (Life Technologies, Carlsbad, Calif.) in a volume of 125 μL with a 20-fold molar excess of label and incubation for 2 h. MBP-Th-RSPO2 was labeled with Alexafluor488 5-TFPE (Life Technologies, Carlsbad, Calif.) in a volume of 2 mL with a 5-fold molar excess of the label and incubation for 45 min. After quenching, the labeled proteins were separated from free label on a PD-10 gel filtration column (GE Healthcare Bio-Sciences, Pittsburgh, Pa.). The equilibrium binding assays were performed as previously described in a buffer containing 50 mM HEPES (pH 7.5), 150 mM NaCl, 0.3%

(v/v) Triton X-100, and 7 mg/ml fatty acid-free BSA (Moad and Pioszak, 2013, op. cit.). Binding data was analyzed with GraphPad Prism5.0 (GraphPad Software, San Diego) as previously described (Moad and Pioszak, 2013, op. cit.).

AlphaLISA® Luminescent Proximity Assay for ZNRF3 ECD Binding. Reaction conditions consisted of 50 mM MOPS pH 7.4, 150 mM NaCl, 7 mg/ml fatty acid-free BSA, 15 or 20 μg/ml each streptavidin-coated donor and anti-MBP antibody-coated acceptor beads (PerkinElmer), 3 nM biotin-ZNRF3 ECD, and the indicated concentrations of MBP-Th-RSPO Fu1-Fu2 proteins. Reactions were prepared in the dark under green light and incubated for 3 h at room temperature in the dark to reach equilibrium. Acceptor bead emission at 615 nm was measured in 384-well white Opti-Plates (Greiner Bio-One North America Inc., Monroe, N.C.) with a POLARstar® Omega plate reader using filters for AlphaLISA® assays (both from BMG Labtech GmbH, Ortenberg, Germany). Values were graphed with GraphPad Prism 5.0 (GraphPad Software, San Diego). AlphaLISA® saturation binding data were not fit by non-linear regression because the two-bead format and consequent multi-valent nature of the assay and the "hook effect" render standard binding equations inappropriate for this assay.

AlphaLISA® Luminescent Proximity Assay for Ternary Complex Formation. Buffer conditions were the same as for the AlphaLISA® ZNRF3 binding assay and the reactions contained 5 nM biotin-ZNRF3 ECD, 5 nM MBP-Th-LGR4 ECD, and the indicated concentrations of MBP-free RSPO Fu1-Fu2 proteins. The reactions were incubated 4 h to reach equilibrium before reading emission at 615 nm as above.

TOPFLASH Wnt/β-Catenin Signaling Reporter Assay. This assay was performed essentially as described (Moad and Pioszak, 2013, op. cit.). HEK293T cells seeded in 96-well cell culture plates in DMEM+10% FBS+50 units/ml penicillin, 50 μg/ml streptomycin were transiently transfected with a plasmid mixture containing 50 ng of Super8× TOPFLASH reporter, 10 ng pRL-TK, and 40 ng empty pcDNA3.1 (per well) using FuGENE® HD transfection reagent (Promega Corp., Madison, Wis.). The recombinant RSPO proteins were dialyzed to PBS, pH 7.4 overnight at 4° C., their concentrations were determined by Bradford assay, and they were diluted as indicated in 1:6 diluted Wnt3a conditioned media. The transfected cells were treated with the proteins for 24 h. Firefly and Renilla luciferase activities were measured with a Dual Luciferase Reporter assay kit (Promega Corp., Madison, Wis.). Signaling response was plotted as the Firefly/Renilla ratio with normalization to controls as indicated. GraphPad Prism 5.0 (GraphPad Software, La Jolla, Calif.) was used for nonlinear regression fitting of the dose-response curves to a three-parameter, fixed slope log(agonist) versus response equation.

Statistical Analysis. Results are presented as the mean+/−standard error of the mean and significance was determined by unpaired t test or ANOVA followed by Tukey's multiple comparisons post hoc test, as appropriate, using GraphPad Prism 5.0 (GraphPad Software, La Jolla, Calif.). In tables, n is the number of observations. In tables and figures, p values are represented as *p<0.05, p<0.01, and *p<0.001.

Amino Acid Sequence Alignments, Structure Analysis, and Figure Preparation. Amino acid sequence alignments were performed with ClustalW2 and sequence alignment figures were generated with ESpript3.0 (Goujon M et al. *Nucleic acids research* (2010) 38: Web Server issue: W695-699; and Robert and Gouet. *Nucleic acids research* (2014) 42: Web Server issue: W320-324). Crystal structure analyses and structure figure preparation used PyMol (Schrödinger, LLC, Cambridge, Mass.).

Results

Figure 1:
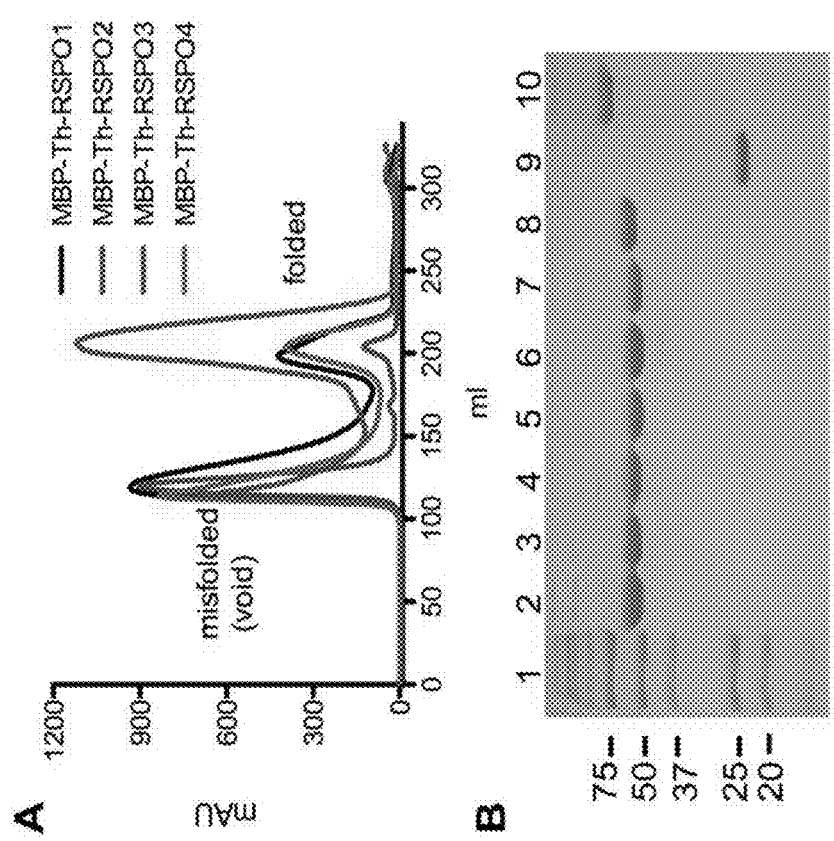
FIG. 1 illustrates recombinant protein production. (A) SUPERDEX® 200 HR gel-filtration chromatograms (GE Healthcare Bio-Sciences, Pittsburgh, Pa.) for the four wild-type MBP-Th-RSPO Fu1-Fu2-$H_6$ proteins produced in $E.$ $coli$. (B) Non-reducing SDS-PAGE showing selected purified proteins used in this study. 2.5 µg of each protein was loaded per lane, and the gel was stained with Coomassie brilliant blue. Molecular mass markers are shown in kDa. Lanes are as follows: 1, marker; 2, MBP-Th-RSPO1 Fu1-Fu2; 3, MBP-Th-RSPO2 Fu1-Fu2; 4, MBP-Th-RSPO3 Fu1-Fu2; 5, MBP-Th-RSPO4 Fu1-Fu2; 6, MBP-Th-RSPO2-4 Fu1-Fu2; 7, MBP-Th-RSPO4-1 Fu1-Fu2; 8, glycosylated MBP-Th-RSPO4 Fu1-Fu2 produced in HEK293T cells; 9, Biotin-ZNRF3 ECD; 10, MBP-Th-LGR4 LRR1-14. All recombinant proteins other than N-glycosylated MBP-Th-RSPO4 Fu1-Fu2 were produced in $E.$ $coli$.

Improved Bacterial Production of Recombinant R-Spondins and Re-Examination of R-Spondin Signaling and Receptor Binding Activities. We previously reported novel methodology for bacterial production of recombinant RSPOs produced as maltose binding protein (MBP)-RSPO Fu1-Fu2-$H_6$ fusion proteins (Moad and Pioszak, 2013, op. cit.). To facilitate additional studies we bacterially expressed and purified the four human RSPO Fu1-Fu2 proteins as MBP-Thrombin cut site (Th)-RSPO Fu1-Fu2-$H_6$ fusion proteins to allow removal of MBP by thrombin digest if necessary. In the course of the studies, changes to the purification protocol were discovered that yielded a marked improvement in the behavior of the RSPO proteins on gel-filtration chromatography as compared to previous results. Degassing the purification buffers and inclusion of 0.5-1 mM EDTA in the buffers allowed us to obtain sharp symmetric "folded" peaks on gel-filtration (FIG. 1(A)) as opposed to the broad asymmetric peaks previously obtained (Moad and Pioszak, 2013, op. cit.). The four resulting MBP-Th-RSPO Fu1-Fu2-$H_6$ proteins were highly purified (FIG. 1(B)).

In light of the improved purifications of the wild-type MBP-Th-RSPO Fu1-Fu2-$H_6$ fusion proteins we re-examined their ability to potentiate low-dose Wnt3a activation of the canonical Wnt/β-catenin pathway in a TOPFLASH dual luciferase reporter signaling assay. The HEK293T cells used for this assay express LGR4, ZNRF3, and Wnt receptors. RSPO2 and RSPO3 exhibited identical strong potencies and maximal responses, RSPO1 exhibited ~6-fold reduced potency compared to RSPO2 and RSPO3 while retaining a similar maximal response, and RSPO4 exhibited a potency slightly stronger than RSPO2 and RSPO3, but a lower maximal response equivalent to ~70% of that observed for RSPO2 and RSPO3 (FIG. 2(A, D, E); Table 1).

TABLE 1

Summary of Signaling Data for Wild-Type RSPOs Fu1-Fu2

| R-spondin | $pEC_{50}$ ± S.E.M. (n) | $E_{max}$ ± S.E.M.[1] (n) |
|---|---|---|
| MBP-Th-RSPO1 | 8.82 ± 0.15** (3) | 88.82 ± 5.05 (3) |
| MBP-Th-RSPO2 | 9.62 ± 0.11 (3) | 100 (3) |
| MBP-Th-RSPO3 | 9.56 ± 0.06 (3) | 101.2 ± 1.39 (3) |
| MBP-Th-RSPO4 | 9.95 ± 0.16 (3) | 67.85 ± 1.07*** (3) |

[1]$E_{max}$ values are % of MBP-Th-RSPO2.
*p < 0.05,
**p < 0.01,
***p < 0.001 versus MBP-Th-RSPO2 by one-way ANOVA with Tukey's Multiple Comparison Test.

In this set of experiments comparing the four wild-type RSPOs to each other, the RSPO4 potency was not statistically significantly different from RSPO2 (Table 1), but in other experiments comparing RSPO2 and RSPO4 to mutant proteins the RSPO2 versus RSPO4 potency difference did reach statistical significance (Table 4). Conservatively speaking, the rank order of potencies was thus RSPO2, RSPO3 and RSPO4>RSPO1 and the rank order of the maximal responses was RSPO1, RSPO2, and RSPO3>RSPO4. These results were consistent with previous results (Moad and Pioszak, 2013, op. cit.), with the exceptions that each of the newly purified RSPOs was a bit more potent and a potency rank order of RSPO2 and RSPO3>RSPO4>RSPO1 was previously observed. Presumably the differences observed in the present work resulted from the improved purification protocol.

The LGR4 ECD binding abilities of the newly purified MBP-Th-RSPO Fu1-Fu2-$H_6$ proteins were examined in an in vitro LanthaScreen®TR-FRET competition-binding assay (Thermo Fisher Scientific Inc., Rockford, Ill.). RSPO4 bound the LGR4 ECD with an affinity ~7-fold stronger than those of RSPO2 and RSPO3, which were equivalent (FIG. 2(B, F); Table 2). RSPO1 affinity for LGR4 was slightly diminished as compared to RSPO2 and RSPO3 (FIG. 2(B, F)), although this did not reach statistical significance by one-way ANOVA and Tukey's test comparing RSPO1 versus RSPO2 or RSPO3. These LGR4 binding data are in agreement with our previous findings (Moad and Pioszak, 2013, op. cit.). Attempts to apply the TR-FRET assay to ZNRF3 binding were unsuccessful (data not shown), so an AlphaLISA® luminescent proximity assay (BMG Labtech GmbH, Ortenberg, Germany) was developed to measure ZNRF3 ECD binding. In this assay, biotinylated ZNRF3 ECD is attached to the surface of streptavidin-coated donor beads and the MBP-Th-RSPO fusion proteins are attached to the surface of α-MBP-coated acceptor beads. Receptor-ligand interaction is detected by measuring 615 nm emission from the acceptor beads, which is dependent on singlet oxygen molecules released from nearby donor beads. Site-specific in vivo biotinylation of the ZNRF3 ECD was carried out by bacterial co-expression of N-terminally Avi-tagged ZNRF3 ECD with the biotin ligase BirA. Biotin-ZNRF3 ECD was purified to homogeneity (FIG. 1(B)). In a saturation binding assay format, RSPO2 and RSPO3 exhibited similar strong binding affinities for ZNRF3, RSPO1 had much weaker affinity, and RSPO4 binding was not detected (FIG. 2(C)), in agreement with our previous findings using a native gel mobility shift assay (Moad and Pioszak, 2013, op. cit.) and with those of Zebisch, et al. using SPR *Nature communications* (2013) 4: 2787).

TABLE 2

Summary of LGR4 ECD Binding Data for Wild Type, Chimeric, and Mutant R-spondins

| R-spondin | $pK_I$ ± S.E.M. (n) |
| --- | --- |
| MBP-Th-RSPO1 | 6.90 ± 0.08*** (3) |
| MBP-Th-RSPO2 | 7.26 ± 0.13*** (4) |
| MBP-Th-RSPO3 | 7.31 ± 0.12*** (3) |
| MBP-Th-RSPO4 | 8.12 ± 0.07 (6) |
| MBP-Th-RSPO2-4 | 8.36 ± 0.04 (3) |
| MBP-Th-RSPO4-1 | 7.32 ± 0.11*** (4) |
| MBP-Th-RSPO2 T111I | 7.57 ± 0.12 (3) |

*$p < 0.05$,
**$p < 0.01$,
***$p < 0.001$ versus MBP-Th-RSPO4 by one-way ANOVA with Tukey's Multiple Comparison Test, except for RSPO2 T111I, which was compared to RSPO2.

Figure 3:
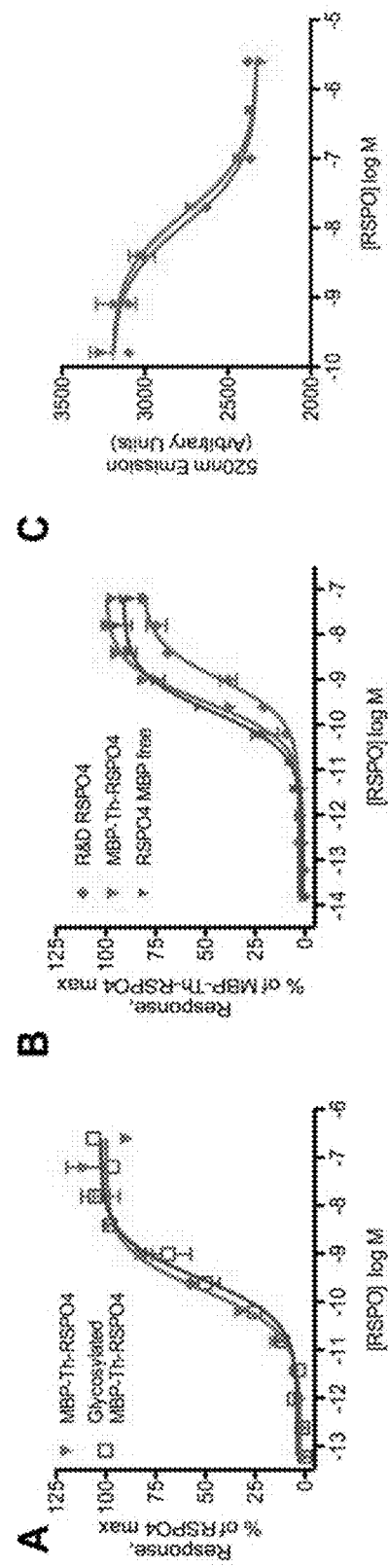
FIG. 3 shows the signaling and LGR4 binding activities of recombinant RSPO4 Fu1-Fu2 proteins produced in bacteria or HEK293T cells and commercial full-length RSPO4 proteins produced in CHO cells. (A) Signaling assay for MBP-Th-RSPO4 Fu1-Fu2 proteins produced in bacteria or HEK293T cells (glycosylated). Data shown are representative of three independent experiments, each performed in duplicate and the error bars represent the S.E.M. of the experiment. (B) Signaling assay for bacterially produced MBP-Th-RSPO4 Fu1-Fu2 and MBP-free RSPO4 Fu1-Fu2 compared to commercial full-length RSPO4 produced in CHO cells (R&D). Data shown are representative of two independent experiments, each performed in duplicate, and the error bars represent the S.E.M. of the experiment. (C) TR-FRET LGR4 ECD competition-binding assay as in FIG. 2(B) comparing bacterially produced MBP-Th-RSPO4 Fu1-Fu2 and commercial full-length RSPO4 (R&D). Data shown are representative of three independent experiments, each performed in duplicate and the error bars represent the S.E.M. of the experiment.

The signaling and receptor binding results with bacterially produced wild-type RSPOs are in good agreement with those of other groups using RSPOs produced in eukaryotic systems with the notable exceptions of the strong signaling potency and strong LGR4 binding affinity of our RSPO4. Other groups reported RSPO4 to have the weakest signaling potency and weakest LGR4 affinity. In the present work, the signaling potency rank order of commercial recombinant RSPO1, RSPO2, and RSPO4 proteins (R&D Systems, Inc., Minneapolis, Minn.) was RSPO2>RSPO1>RSPO4 consistent with the findings of other groups (FIG. 11). The commercial RSPO1 and RSPO4 proteins are full-length, whereas RSPO2 is the Fu1-Fu2-TSP fragment. Seeking the source of the RSPO4 discrepancy, N-glycosylated MBP-Th-RSPO4 Fu1-Fu2-$H_6$ secreted from HEK293T cells (FIG. 1(B)) was expressed and purified and compared its signaling activity to that of the equivalent bacterially produced protein. The HEK293T cell-produced protein exhibited signaling potency and efficacy similar to the bacterially produced protein (FIG. 3(A); Table 3). A sensitive t-test indicated that the $pEC_{50}$ values were statistically significantly different, but the effect was not dramatic and did not appear to be sufficient to account for the discrepancy. Comparing the signaling activities of bacterially produced MBP-Th-RSPO4 Fu1-Fu2, MBP-free RSPO4 Fu1-Fu2 (generated by thrombin cleavage of the bacterially produced protein and purification of the Fu1-Fu2 fragment), and R&D Systems, Inc. (Minneapolis, Minn.) full-length RSPO4 indicated that MBP did not alter signaling potency and that the minimal Fu1-Fu2 domain module proteins were more potent than the full-length protein (FIG. 3(B)). Notably, the commercial full-length RSPO4 exhibited LGR4 ECD binding affinity identical to bacterially produced MBP-Th-RSPO4 Fu1-Fu2 (FIG. 3(C); Table 3). These data indicate the RSPO4 TSP domain and/or C-terminal basic region may have an inhibitory effect on RSPO4 signaling activity, which may explain the discrepancy.

TABLE 3

Summary of Signaling and LGR4 ECD Binding Data for RSPO4 Proteins Produced in Different Expression Systems

| R-spondin (expression system) | $pEC_{50}$ ± S.E.M. (n) | $E_{max}$ ± S.E.M.[1] (n) | $pK_I$ ± S.E.M. (n) |
| --- | --- | --- | --- |
| MBP-Th-RSPO4[2] (E. coli) | 9.80 ± 0.04 (3) | 100 (3) | 8.28 ± 0.14 (3) |
| MBP-Th-RSPO4[2] (HEK293T) | 9.48 ± 0.04** (3) | 94.77 ± 4.63 (3) | — |
| R&D RSPO4[3] (CHO) | — | — | 8.23 ± 0.11 (3) |

[1]$E_{max}$ values are % of bacterially produced MBP-Th-RSPO4.
[2]Fu1-Fu2 domain module.
[3]Full-length protein.
*$p < 0.05$,
**$p < 0.01$,
***$p < 0.001$ versus bacterially produced MBP-Th-RSPO4 by unpaired t test.

Engineering a Highly Potent and Efficacious Chimeric "Superspondin." An R-spondin variant ("RSPO2-4") was constructed by combining the ZNRF3 binding portion of RSPO2 with the LGR4 binding portion of RSPO4 in the form of a chimeric MBP-Th-RSPO2-4 Fu1-Fu2 molecule. Chimera design was aided by consulting the crystal structure of the ternary RSPO1 Fu1-Fu2:LGR5 ECD:RNF43 ECD complex (FIG. 4(A)) and an amino acid sequence alignment of the four wild type RSPOs (FIG. 12). The design resulted in a chimeric RSPO2-4 Fu1-Fu2 molecule with a junction point between the $2^{nd}$ and $3^{rd}$ β-hairpin structural elements of Fu1 such that the ZNRF3 interacting region of RSPO2 was fused to the LGR4 interacting region of RSPO4 (FIG. 4(B)). The bacterially produced recombinant MBP-Th-RSPO2-4 Fu1-Fu2 chimera exhibited 10-fold stronger signaling potency than RSPO2 and efficacy equivalent to RSPO2 (FIG. 5(A, D, E); Table 4). The RSPO2-4 chimera bound the ZNRF3 (FIG. 5(B)) and LGR4 (FIG. 5(C, F); Table 2) ECDs with affinities similar to RSPO2 and RSPO4, respectively.

TABLE 4

Summary of Signaling Data for RSPO2-4 Chimera and Mutants

| R-spondin | pEC$_{50}$ ± S.E.M. (n) | E$_{max}$ ± S.E.M.[1] (n) |
|---|---|---|
| MBP-Th-RSPO2 | 9.43 ± 0.08 (7) | 100 (7) |
| MBP-Th-RSPO4 | 9.86 ± 0.08** (5) | 74.14 ± 2.62*** (5) |
| MBP-Th-RSPO2-4 | 10.45 ± 0.05*** (7) | 105.9 ± 2.78 (7) |
| MBP-Th-RSPO4-triple | 10.19 ± 0.16*** (4) | 97.94 ± 7.51 (4) |
| MBP-Th-RSPO2[2] | 9.37 ± 0.08 (3) | 100 (3) |
| MBP-Th-RSPO4[2] | 9.69 ± 0.04* (3) | 74.25 ± 2.26*** (3) |
| MBP-Th-RSPO2 T111I[2] | 9.75 ± 0.07* (3) | 103.1 ± 2.40 (3) |

[1]E$_{max}$ values are % of MBP-Th-RSPO2.
[2]RSPO2 T111I was compared to RSPO2 and RSPO4 in a separate set of experiments so the controls are listed twice.
*p < 0.05,
**p < 0.01,
***p < 0.001 versus MBP-Th-RSPO2 by one-way ANOVA with Tukey's Multiple Comparison Test.

An AlphaLISA® assay (BMG Labtech GmbH, Ortenberg, Germany) was developed to allow direct assessment of ternary complex formation. This assay was similar to the ZNRF3 ECD binding assay, except that MBP-Th-LGR4 ECD was attached to the surface of the α-MBP-coated acceptor beads and MBP-free RSPO Fu1-Fu2 proteins were used to bring the receptor-coated beads into proximity. MBP-free RSPO2-4 chimera and RSPO2 were generated by thrombin digestion of their respective fusion proteins followed by purification to isolate the RSPO Fu1-Fu2. A gel-filtration chromatography step was included in the purifications to eliminate the possibility of contaminating undigested MBP-Th-RSPO fusion protein. In a saturation binding assay format, the RSPO2-4 chimera exhibited enhanced ability to bring the two receptors together as compared to RSPO2 (FIG. 6). Control experiments indicated that the two receptors did not associate in the absence of RSPOs and signal generation was dependent on the presence of both receptors (FIG. 13). These results suggested that the enhanced signaling potency of the RSPO2-4 chimera resulted from its increased ability to form the ternary complex.

Engineering a Low Potency, Low Efficacy Chimeric "Poorspondin." It was hypothesized that a chimeric RSPO4-1 molecule combining the poor ZNRF3 binding of RSPO4 with the weak LGR4 binding of RSPO1 should be a "Poorspondin" with weak signaling potency and efficacy. To test this hypothesis, a MBP-Th-RSPO4-1 Fu1-Fu2 chimera was constructed and tested. The chimera junction point was the same as for the Superspondin RSPO2-4 (FIG. 4(B)). The bacterially produced recombinant MBP-Th-RSPO4-1 Fu1-Fu2 chimera exhibited potency in the signaling assay similar to RSPO1 and efficacy equivalent to that of RSPO4 (FIG. 7(A, C, D); Table 5). The RSPO4-1 variant bound the LGR4 ECD with significantly weaker affinity than RSPO4, but unexpectedly it retained slightly better binding affinity for LGR4 than RSPO1 (FIG. 7(B, E); Table 2). The difference in mean pK$_1$ values for RSPO1 versus the RSPO4-1 chimera was statistically significant (p<0.05) as assessed by one-way ANOVA with Tukey's post test.

TABLE 5

Summary of Signaling Data for RSPO4-1 Chimera

| R-spondin | pEC$_{50}$ ± S.E.M. (n) | E$_{max}$ ± S.E.M.[1] (n) |
|---|---|---|
| MBP-Th-RSPO1 | 8.66 ± 0.05 (3) | 100 (3) |
| MBP-Th-RSPO4 | 9.80 ± 0.04*** (3) | 77.45 ± 1.36*** (3) |
| MBP-Th-RSPO4-1 | 8.79 ± 0.05 (3) | 81.06 ± 2.31*** (3) |

[1]E$_{max}$ values are % of MBP-Th-RSPO1.
*p < 0.05,
**p < 0.01,
***p < 0.001 versus MBP-Th-RSPO1 by one-way ANOVA with Tukey's Multiple Comparison Test.

Enhancing Signaling Potency by Introducing Amino Acid Substitutions into RSPO4 or RSPO2. Amino acid substitutions which could confer upon RSPO4 the strong ZNRF3 binding of RSPO2 were sought. The crystal structures of the binary RSPO1 and -2 Fu1-Fu2:ZNRF3 ECD complexes (FIG. 8(A)) and an amino acid sequence alignment of the four human RSPOs for the ZNRF3/RNF43-interacting region, which is comprised of the first two β-hairpin structural elements of Fu1 (FIG. 8(B)) were analyzed. The structures and mutagenesis data indicated that two conserved RSPO residues are most critical for ZNRF3/RNF43 binding: R66 and Q71 (based on RSPO1 sequence numbering), which are located on the β-strands of the 2$^{nd}$ β-hairpin of Fu1 and face into a shallow cleft on the ZNRF3/RNF43 surface (FIGS. 4(B) and 8(A)). RSPO1-4 have a variable residue at position 69 (RSPO1 numbering) on the tip of the loop of the 2$^{nd}$ β-hairpin of Fu1 (FIG. 8(B)). This residue, either an isoleucine or a methionine, fits into a hydrophobic pocket of ZNRF3 formed by residues 198, V195, and A201. Methionine at this position was previously shown to contribute to the increased ZNRF3 binding affinity of RSPO2, but not enough to account for the dramatic difference in ZNRF3/RNF43 binding affinities of RSPO2 and RSPO3 as compared to RSPO1 and RSPO4. Two additional residues in RSPO β-strand 3 at positions 62 and 64 (RSPO1 numbering) provide contacts to ZNRF3 and differ among the four RSPOs (FIG. 8(B)). RSPO4 residues L56 and I58 were reasoned to provide less favorable contacts with ZNRF3 L104 and H102 than RSPO2 F61 and L63. Indeed, the recombinant MBP-Th-RSPO4 Fu1-Fu2-H$_6$ [L56F/I58L/I63M]triple mutant exhibited enhanced ZNRF3 binding (FIG. 8(C)), albeit not as strong as RSPO2 or the 2-4 chimera, and signaling potency ~6-fold stronger than RSPO2 and efficacy equivalent to RSPO2 (FIG. 8(D); Table 4).

The success at generating enhanced signaling potency and efficacy of RSPO4 by introducing a small number of amino acid substitutions provided encouragement to seek substitutions in RSPO2 that would confer upon it the strong LGR4 binding of RSPO4 and thereby enhance its signaling potency. To understand the structural basis for the high-affinity LGR4 binding of RSPO4 and rationalize why RSPOs1-3 have weaker LGR4 affinity the crystal structure of the binary RSPO1 Fu1-Fu2:LGR4 ECD complex (FIG. 14(A)) and an amino acid sequence alignment of the four human RSPOs for the LGR4/5/6-interacting region, which is comprised primarily of the third β-hairpin of Fu1 and the first β-hairpin of Fu2 (FIG. 14(B)) was investigated. The structures and mutagenesis data indicated three conserved RSPO residues important for LGR binding: R87 (RSPO1 numbering), which is located at the end of β-strand 5 in the third β-hairpin of Fu1, and F106 and F110, which are situated on the loop of the first β-hairpin of Fu2 (FIGS. 4(B) and 14(B)). R87 forms salt-bridge and/or hydrogen bonds with a cluster of aspartate residues in LGR4 (D137, 161, and 162), whereas F106 and F110 form hydrophobic interactions with W159, A181, V204, and V205 of LGR4. RSPO1 T112, which is adjacent to F106 and F110, is conserved in RSPO1-3, but this position is an isoleucine in RSPO4. It was reasoned that an isoleucine at this position might provide additional hydrophobic/van der Waals contacts to LGR4 W159 and/or H157 to provide a stronger binding affinity (FIG. 14(A)). The recombinant MBP-Th-RSPO2 Fu1-Fu2-H$_6$ [T111I] mutant exhibited LGR4 binding affinity that was not statistically significantly different from that of RSPO2 (Table 2), although the trend was towards improved LGR4 affinity (FIG. 14(C, E)). The RSPO2 [T111I] mutant exhibited slightly stronger signaling potency than RSPO2 and this result did reach statistical significance (Table 4), but it was not a dramatic effect (FIG. 14 (D, F, G)). In the course of these experiments, the RSPO2 S77D single and S77D/P88Q/K107Q triple mutant proteins were also constructed and tested, and were chosen as candidates for increased LGR4 affinity based on sequence alignment and structural considerations, but these mutants did not exhibit enhanced signaling potencies (data not shown).

In at least one embodiment, the present disclosure includes an R-spondin chimeric protein ("RSPO2-4 variant") comprising at least a portion of the Fu1 domain of R-spondin-2 (RSPO2) and at least a portion of the Fu2 domain of R-spondin-4 (RSPO4), for example as shown in SEQ ID NO:9, wherein amino acids 1-55 comprise amino acids 22-76 of RSPO2 (SEQ ID NO:2) and amino acids 56-122 comprise amino acids 72-138 of RSPO4 (SEQ ID NO:4). In this embodiment, amino acids 56-74, which include the beta 5 and beta 6 strands of Fu1 (see FIG. 12)) are derived from the Fu1 domain of RSPO4 (not from the Fu1 domain of RSPO2). FIG. 9 shows SEQ ID NO:9. Amino acids 56-74, the portion of Fu1 which comprises the beta 5 and beta 6 strands (see FIG. 12), are indicated in italics. As noted, this portion of the Fu1 domain is derived from RSPO4, rather than from the Fu1 domain of RSPO2. The boldfaced residues (at positions 56, 59, 62, 64, 66-69, and 73-74) indicate residues of RSPO4 Fu1 which differ from corresponding residues of RSPO2 Fu1. The corresponding RSPO2 Fu1 residues are indicated in boldface below the RSPO4 residues. In other non-limiting embodiments, the RSPO2-4 chimera comprises a sequence wherein at least one of amino acid positions D56, P59, F62, 164, G66, Q67, E68, V69, K73 and K74 of SEQ ID NO:9 is substituted with an amino acid from a corresponding position of RSPO1, RSPO2, or RSPO3. For example, in certain embodiments, one or more of positions 56, 59, 62, 64, 66, 67, 68, 69, 73 and 74 of SEQ ID NO:9 can be replaced with amino acids S, S, Y, H, A, P, D, M, A, or R, respectively (from corresponding positions in RSPO2). In alternate non-limiting embodiments, position 56 may be replaced with N or E, and/or position 59 may be replaced with G, and/or position 62 may be replaced with L, M, or W, and/or position 64 may be replaced with L, M, T, or V, and/or position 66 may be replaced with P, Y, or S, and/or position 67 may be replaced with A, N, E, H, K, or M, and/or position 68 may be replaced with Q, or K, and/or position 69 may be replaced with I or L, and/or position 73 may be replaced with R, S, T, N, Q, or E, and/or position 74 may be replaced with N, Q, or E.

At least one embodiment of the present disclosure includes an R-spondin chimeric protein ("RSPO3-4 variant") comprising at least a portion of the Fu1 domain of R-spondin 3 (RSPO3) and at least a portion of the Fu2 domain of R-spondin-4 (RSPO4), for example as shown in SEQ ID NO:10, wherein amino acids 1-57 comprise amino acids 22-78 of RSPO3 (SEQ ID NO:3) and amino acids 58-124 comprise amino acids 72-138 of RSPO4 (SEQ ID NO:4). In this embodiment, amino acids 58-76, which include the beta 5 and beta 6 strands of Fu1 (see FIG. 12) are derived from the Fu1 domain of RSPO4 (not from the Fu1 domain of RSPO3). FIG. 10 shows SEQ ID NO:10. Amino acids 58-76, the portion of Fu1 which comprises the beta 5 and beta 6 strands (see FIG. 12), are indicated in italics. As noted, this portion of the Fu1 domain is derived from RSPO4, rather than from the Fu1 domain of RSPO3. The boldfaced residues (at positions 58, 61, 64, 66, 68-71, and 75) indicate residues of RSPO4 Fu1 which differ from corresponding residues of RSPO3 Fu1. The corresponding RSPO3 Fu1 residues are indicated in boldface below the RSPO4 residues. In other non-limiting embodiments, the RSPO3-4 chimera comprises a sequence wherein at least one of amino acid positions D58, P61, F64, 166, G68, Q69, E70, V71, and K75 of SEQ ID NO:10 is substituted with an amino acid from a corresponding position of RSPO1, RSPO2, or RSPO3. For example, one or more of positions 58, 61, 64, 66, 68-71, and 75 of SEQ ID NO:10 can be replaced with amino acids S, S, Y, T, Y, P, D, I and T, respectively (from corresponding positions of RSPO3). In alternate non-limiting embodiments, position 58 may be replaced with N or E, and/or position 61 may be replaced with G, and/or position 64 may be replaced with L, M, or W, and/or position 66 may be replaced with H, L, M, or V, and/or position 68 may be replaced with P, A or S, and/or position 69 may be replaced with A, N, E, H, K, or M, and/or position 70 may be replaced with Q, or K, and/or position 71 may be replaced with I, M or L, and/or position 75 may be replaced with A, R, S, N, Q, or E.

At least one embodiment of the present disclosure includes an R-spondin-4 mutant protein ("RSPO4 triple mutant") comprising Fu1 and Fu2 of RSPO4 (amino acids 21-138 of SEQ ID NO:4) wherein the amino acids L, I, and I in positions 56, 58, and 63, respectively are substituted. In a specific embodiment, represented as SEQ ID NO:14, positions 56, 58, and 63 of SEQ ID NO:4 have been substituted with F, L, and M, respectively. Various embodiments include, but are not limited to, RSPO4 triple mutants where position 56 is substituted with V, F, M, or W, position 58 is substituted with V, L, F, M, or W, and position 63 is substituted with V, L, F, M or W.

Certain embodiments of the present disclosure include an R-spondin-2 mutant protein comprising Fu1 and Fu2 of RSPO2 (amino acids 22-144 of SEQ ID NO:2), wherein the amino acid T in position 111 is substituted. In a specific embodiment, represented as SEQ ID NO:15, position 111 of SEQ ID NO:2 has been substituted with I. In alternate non-limiting embodiments, T in position 111 can be substituted with any one of V, L, M, F, or W. In certain embodiments, the present disclosure is directed to an R-spondin-3 mutant protein comprising Fu1 and Fu2 of RSPO3 (amino acids 22-146 of SEQ ID NO:3), wherein the amino acid T in position 112 is substituted. In a specific embodiment, represented as SEQ ID NO:17, position 112 of SEQ ID NO:3 has been substituted with I. In alternate non-limiting embodiments, T in position 112 can be substituted with any one of V, L, M, F, or W.

The R-spondin Fu1-Fu2 variants (chimeras and mutants) described herein may comprise an R-Spondin TSP region, such as one of SEQ ID NOS. 20-22 and/or one of R-spondin C-terminal basic regions SEQ ID NOS: 23 or 24. Non-limiting examples of such Fu1-Fu2 chimeras include SEQ ID NOS:25-29.

The R-spondin variants of the present disclosure have, but are not limited to, at least two utilities. The first is their use for regenerative medicine applications based on their function as growth factors for cells responsive to R-spondins. Researchers developed an in vitro cell culture system in which isolated R-spondin-responsive cells such as, but not limited to, adult intestinal stem cells, colon cells, esophagus cells, small intestine cells, ovary cells, prostate cells, liver cells, and pancreas cells can be coaxed to grow into "organoids" (e.g., "mini-guts") in the lab. These culture systems can serve as a source of tissue for transplant into patients. Recombinant R-spondin protein is an important component of the cell culture media that is used for such organoid cultures. The high-potency "Superspondins" of the present disclosure permit organoid culture with a smaller quantity of R-spondin protein, thereby providing cost-savings over the prior technology which relies on costly recombinant wild type R-spondins. In certain embodiments, the RSPO variants of the present disclosure may be used in cell culture media and under culturing conditions disclosed in U.S. Pat. No. 8,642,339 (e.g., in Example 1, Col. 24-29), which is incorporated herein by reference in its entirety. In non-limiting embodiments, the R-spondin variants of the present disclosure, when in a cell culture medium, may be present therein at a concentration in a range, for example, from about 0.1 nM to about 1000 nM. In certain non-limiting embodiments, the RSPO2-4 ("Superspondin") variant is present at a concentration in a range of from about 0.2 nM to about 500 nM, and the RSPO4-1 ("Poorspondin") variant is present at a concentration in a range of from about 2 nM to about 1000 nM.

A series of experiments were conducted in which recombinant wild type RSPOs and novel RSPO variants of the present disclosure were used in a culture medium (Table 6) to culture organoids, as described below.

The recombinant, $E.\ coli$-produced RSPO Fu1-Fu2-$H_6$ proteins were tested for their ability to support mouse small intestine organoid culture using the conditions developed by Sato and Clevers (*Nature* (2009) 459(7244):262-5). Organoid culture is a physiologically relevant culture system wherein the R-spondins function at the relevant cell types that express LGR4/5 and ZNRF3/RNF43 receptors, i.e. crypt base columnar stem cells. For these experiments the RSPO proteins were produced free of MBP as previously described (Warner, et al. *Mol Pharmacology* (2015) 87(3): 410-20) and further processed to deplete endotoxin. The $E.\ coli$-produced RSPO Fu1-Fu2-$H_6$ proteins including RSPO1, RSPO2, RSPO4, RSPO2-4 variant ("Superspondin"), and RSPO4-1 variant ("Poorspondin"), as well as full-length RSPO1 produced in CHO cells purchased from R&D Systems, Inc. (Minneapolis, Minn.), were examined for their abilities to support primary organoid culture as well as the passaging of organoid cultures.

Crypt Isolation and Culture

The following protocol was developed via a number of procedures from various groups (Sato and Clevers, *Methods Mol Biol*. (2013) 945:319-28; Bas and Augenlicht, *J Vis Exp* (2014) 93:e52026; and Mahe et al., *Curr Protoc Mouse Biol*. (2013) 3(4):217-40).

Isolation of Crypts from the Small Intestine: All steps were carried out under sterile conditions in laminar flow hood:

1. Isolated intestines from C57BL6 mice (provided by Dr. Ann-Louise Olson (University of Oklahoma Health Sciences Center, Oklahoma City, Okla.) under her IACUC protocol 14-007). Euthanized the mice with $CO_2$, followed by cervical dislocation.
2. Opened up the abdomen longitudinally and filled the small intestine (SI) with ice-cold phosphate buffered saline, PBS (—$Ca^{2+}$; —$Mg^{2+}$) with 2× antibiotic-antimycotic (optional). Rapidly isolated small intestine.
3. Thoroughly dissected free of mesenteric fat using a scalpel. Be careful not to perforate the tissue—at all times the tissue was kept moist with ice cold PBS. Opened up intestine longitudinally and washed thoroughly with ice cold PBS.
4. Cut small intestine into two sections and flattened out using a wet cotton tip, gently scraped off the villi using a pre-cooled slide. Washed in ice-cold PBS.
5. Cut tissue into small pieces (2-4 mm) using a razor blade on a pre-cooled slide. Transferred the pieces into a 50 ml tube containing 20 ml ice cold PBS.
6. Pipetted up and down gently 10× using a 10 ml sterile disposable pipette. Let tissue fragments sediment by gravity. Removed the supernatant with a pipette. Repeated three additional times or until supernatant is almost clear.
7. Added 30 ml of ice-cold crypt isolation buffer and incubated at 4° C. for 30 minutes with gentle rocking.
8. Let tissue sediment and discarded supernatant. Added 15 ml ice cold PBS and pipetted up and down 5× with a 10 ml pipette. Let the tissue fragments sediment and collected the supernatant as Fraction 1 (F1). Repeated collecting F2-F3, each fraction maintained separately.
9. Added 15 ml ice cold PBS, and this time shook vigorously by hand for 15 sec. Collected F4 and repeated for F5, F6. If tissue pieces start to float, tapped to help them settle.
10. Inspected an aliquot of each fraction under the microscope. Pooled those fractions containing crypts (typically F3 and on).
11. Passed the pooled fractions through a 70 µm nylon cell strainer, collecting crypts in a BSA coated 50 ml tube.
12. Centrifuged at 300×g for 5 minutes at 4° C., discarded the supernatant.

Resuspended pellet in 10 ml ice-cold basal culture medium and transferred to a 15 ml tube.

13. Centrifuged at 200×g for 2 minutes and removed supernatant to remove single cells. Resuspended again in 10 ml ice-cold basal culture media.
14. Counted the crypts using a hemocytometer (10 µl from 10 ml crypts suspension, total number of crypts=number of crypts counted×1000).
15. Centrifuged crypts at 100×g for 5 minutes at 4° C. and removed supernatant. Resuspended crypts in MATRIGEL® matrix (Corning Inc., Tewksbury, Mass.) (200-500 crypts/50 µl).
16. Plated 50 µl of crypt—MATRIGEL® suspension per well in a pre-warmed 24-well plate (growth area: 2 $cm^2$), carefully placing the drop in the center of each well. Transferred the plate in a $CO_2$, 37° C. incubator for ~10 minutes until the suspension solidified.
17. Added 500 µl room temp Complete culture media/well (see Table 6 for Complete culture media). Incubated in 5% $CO_2$, 37° C.
18. Exchanged culture media with fresh, every 4-6 days.

TABLE 6

| Complete Culture Media: Growth Factors (Noggin, EGF, and R-spondins) Were Re-constituted in Sterile 1X PBS + 0.1% BSA | | |
|---|---|---|
| Ingredient | Final Concentration | Company/Cat. # |
| Advanced DMEM/F12 | 1X | Life Technologies/12634-010 |
| B-27 supplement | 1X | Life Technologies/12587-010 |

TABLE 6-continued

Complete Culture Media: Growth Factors (Noggin, EGF, and R-spondins)
Were Re-constituted in Sterile 1X PBS + 0.1% BSA

| Ingredient | Final Concentration | Company/Cat. # |
|---|---|---|
| N-2 supplement | 1X | Life Technologies/17502-048 |
| N-acetyl-L-cysteine | 1 mM | Sigma/A9165 |
| GIBCO ® GlutaMAX ™ media* | 2 mM | Life Technologies/35050-061 |
| Hepes pH 7.5 | 10 mM | Sigma/H4034 |
| Penicillin-Streptomycin | 100 µg/ml-100 µg/ml | Life Technologies/15070-063 |
| Recombinant Murine Noggin | 100 ng/ml | Peprotech/250-38 |
| Recombinant Mouse EGF | 50 ng/ml | Life Technologies/PMG8045 |
| Recombinant Human R-Spondin-1** | 750 ng/ml (~20 nM) | R&D Systems***/4645-RS-025/CF |

*Thermo Fisher Scientific Inc., Rockford, IL
**Bacterial produced R-Spondin variants of the present disclosure were used at varied concentrations in place of the R&D Systems R-Spondin-1.
***R&D Systems, Inc. (Minneapolis, MN)

Testing Fu1-Fu2 RSPO Proteins in Organoid Culture

Isolated crypts were incubated in the Complete culture media containing either RSPO1, RSPO2, RSPO4, RSPO2-4 variant, or RSPO4-1 variant. The RSPO proteins were diluted in sterile 1×PBS with 0.1% BSA before addition to complete culture media. Concentrations used to test the bacterial RSPOs were as follows: RSPO1: 0.02 nM, 0.2 nM, 2 nM, 20 nM, and 200 nM; RSPO2: 0.02 nM, 0.2 nM, 2 nM, 20 nM, and 200 nM; RSPO2-4: 0.02 nM, 0.2 nM, 2 nM, 20 nM, and 200 nM; RSPO4-1: 20 nM and 200 nM; RSPO4: 20 nM. Organoid growth was tracked over a five day period using a Nikon microscope for live-cell brightfield imaging with 5% $CO_2$ and 37° C. incubation. Images were taken every 3 hours.

The RSPO2-4 variant supported robust organoid growth at a concentration of 2 nM and gave rise to budding crypt structures faster than the next most active R-spondin, RSPO2, when followed over the first 5 days of culture (FIG. 15A and FIG. 15B). Following the cultures out to 11 days of growth revealed that RSPO1, RSPO2, and the RSPO2-4 variant all supported organoid growth at 2 nM, but the RSPO2-4 variant-cultured organoids generally had more budding crypt structures (FIG. 16). RSPO1 and RSPO2 at 0.2 nM were unable to support organoid growth, whereas the RSPO2-4 variant showed the beginnings of a budding structure at this concentration (FIG. 17), indicating an enhanced ability of the RSPO2-4 variant to support organoid culture over RSPO1 and RSPO2.

Testing of the various RSPO proteins at a concentration of 20 nM revealed that *E. coli*-produced RSPO1, RSPO2, and the RSPO2-4 variant supported organoid growth better than full-length RSPO1 purchased from R&D Systems, Inc. (Minneapolis, Minn.) (FIG. 18). The RSPO2-4 variant at 20 nM appeared to favor more and longer budding crypt structures than RSPO1 and RSPO2. RSPO4 was able to support organoid growth to a lesser extent. Notably, the RSPO4-1 variant was unable to support organoid growth at 20 nM (FIG. 18(G)), but did support growth at 200 nM (FIG. 18(H)). Thus, the behavior of the RSPO4-1 variant in organoid culture mirrored its activity in the cell-based TOPFLASH Wnt signaling assay. The abilities of *E. coli*-produced RSPO1, RSPO2, and the RSPO2-4 variant to support the passaging of organoid cultures were further assessed. All three proteins were capable of supporting passaging at a concentration of 2 nM. The RSPO2-4 variant performed better than RSPO1 and RSPO2 at supporting growth of passaged organoids when compared at the low concentration of 0.8 nM.

Overall, the organoid culture experiments indicated that *E. coli*-produced RSPO Fu1-Fu2-$H_6$ proteins support robust organoid growth. More importantly, the enhanced organoid growth in the presence of the RSPO2-4 variant and the decreased organoid growth in the presence of the RSPO4-1 variant indicated good agreement between the pharmacological activities of the proteins in the TOPFLASH Wnt signaling assay and the physiologically relevant organoid culture system. The RSPO2-4 variant is thus an ideal protein to be used for organoid culture and thereby regenerative medicine applications because it can support robust organoid growth better than the wild-type R-spondins.

A second use of R-spondins of the present disclosure is in therapy, for example (but not by way of limitation) in colitis protection, against chemotherapy and radiation therapy-induced tissue damage, including but not limited to, radiation-induced gastrointestinal syndrome (RIGS), systemic graft-versus-host disease, and oral mucositis. Further, in certain embodiments, the higher potency of the variant RSPOs of the present disclosure enables their use at lower doses or levels than other R-spondins.

Practice of the methods of the present disclosure may comprise administering to a subject a therapeutically effective amount of the protein compound in any suitable systemic and/or local formulation, in an amount effective to deliver the dosages listed herein. A therapeutically effective amount of an R-spondin protein of the present disclosure will generally contain sufficient active substance to deliver, in certain embodiments, from about 0.1 µg/kg to about 100 mg/kg (mass of R-spondin/body weight of the subject). Particularly, the composition will deliver about 0.5 µg/kg to about 50 mg/kg, and more particularly about 1 µg/kg to about 10 mg/kg. The dosage can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method, the protein or peptide compound is provided in an IV infusion in the range of from about 0.1 µg/kg to about 10 mg/kg of body weight once a day.

Administration of the protein or peptide compound used in the pharmaceutical composition or to practice the method of the present disclosure can be carried out in a variety of conventional ways, such as, but not limited to, orally, by inhalation, rectally, or by cutaneous, subcutaneous, intraperitoneal, vaginal, or intravenous injection. Oral formulations may be formulated such that the protein compound passes through a portion of the digestive system before being released; for example (but not by way of limitation), it may not be released until reaching the small intestine or the colon.

When a therapeutically effective amount of the protein is administered orally, it may be in the form of a solid or liquid preparation, such as (but not limited to) capsules, pills, tablets, lozenges, melts, powders, suspensions, solutions, elixirs, or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition may contain a solid carrier, such as a gelatin or an adjuvant. The tablet, capsule, and powder may contain from about 0.05% to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution; dextrose or other saccharide solution; or glycols such as (but not limited to) ethylene glycol, propylene glycol, or polyethylene glycol. When administered in liquid form, the pharmaceutical composition particularly contains from about 0.005% to about 95% by weight of the active substance. For example, a dose of about 10 mg to about 1000 mg once or twice a day could be administered orally.

In another embodiment, the proteins of the present disclosure can be tableted with conventional tablet bases such as lactose, sucrose, and cornstarch in combination with binders, such as (but not limited to) acacia, cornstarch, or gelatin; disintegrating agents, such as (but not limited to) potato starch or alginic acid; and a lubricant, such as (but not limited to) stearic acid or magnesium stearate. Liquid preparations may be prepared by dissolving the protein compound in an aqueous or non-aqueous pharmaceutically acceptable solvent which may also contain suspending agents, sweetening agents, flavoring agents, and preservative agents as are known in the art.

For parenteral administration, for example, the protein of the present disclosure may be disposed in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives and buffers as are known in the art.

When a therapeutically effective amount of the protein is administered by intravenous, cutaneous, or subcutaneous injection, the protein may be in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the protein, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the protein compound selected, the infection to be treated, the stage of the infection, and other relevant circumstances using formulation technology known in the art, described, for example, in *Remington: The Science and Practice of Pharmacy*, 21$^{st}$ ed.

Additional pharmaceutical methods may be employed to control the duration of action of the protein. Increased half-life and/or controlled release preparations may be achieved through the use of polymers to conjugate, complex with, and/or absorb the active substance described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release. The protein may also be ionically or covalently conjugated to the macromolecules described above.

Another possible method useful in controlling the duration of action of the protein by controlled release preparations and half-life is incorporation of the protein compound or its functional derivatives into particles of a polymeric material such as polyesters, polyamides, polyamino acids, hydrogels, poly(lactic acid), ethylene vinylacetate copolymers, copolymer micelles of, for example, polyethylene glycol (PEG) and poly(1-aspartamide). The protein may also be ionically or covalently conjugated to the macromolecules described above, particularly PEG of various molecular weights. In certain embodiments the proteins may be covalently linked at a suitable functional group such as the N-terminal end thereof to one or more PEG molecules to form a "PEGylated" protein or peptide. Examples of PEG molecules that can be used include, but are not limited to, a "mini-PEG™" molecule comprising AEEA and/or AEEEA. AEEA is [2-(2-amino-ethoxy)-ethoxy]-acetic acid (also known as 8-Amino-3,6-Dioxaoctanoic acid), and AEEEA is {2-[2-(2-amino-ethoxy)-ethoxy]-ethoxy}-acetic acid (also known as 11-Amino-3,6,9-Trioxaundecanoic acid). The PEG molecule may have a molecular weight (MW) in a range of from about 350 Daltons to about 20,000 Daltons. More particularly, the PEG molecule may have a MW in a range of from about 450 Da to about 15,000 Da. More particularly, the PEG molecule may have a MW in a range of from about 1000 Da to about 12,000 Da. More particularly, the PEG molecule may have a MW in a range of from about 2000 Da to about 10,000 Da. More particularly, the PEG molecule may have a MW in a range of from about 3000 Da to about 8,000 Da.

It is also possible to entrap the protein compounds in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the protein is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the US Food and Drug Administration (Silver Spring, Md.), which are readily available to those in the field. The pharmaceutical composition may also be in the form of an aqueous solution containing many of the same substances as described above for the reconstitution of a lyophilized product.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure.

Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. An R-spondin variant, comprising:
a ZNRF3 binding region of a first R-spondin, the ZNRF3 binding region comprising an amino acid sequence having at least 90% identity to amino acids 22-76 of SEQ ID NO:2 or to amino acids 22-78 of SEQ ID NO:3;
an LGR4 binding region of a second R-spondin, the LGR4 binding region comprising an amino acid sequence having at least 90% identity to amino acids 72-138 of SEQ ID NO:4; and
wherein the R-spondin variant has ZNRF3 and LGR4 binding activity.

2. An R-spondin variant, comprising:
(1) a ZNRF3 binding region of a first R-spondin, the ZNRF3 binding region comprising:
an amino acid sequence having at least 90% identity to amino acids 22-144 of SEQ ID NO:2 and comprising one or more substitutions thereto, wherein the amino acid T in position 111 is substituted; or
an amino acid sequence having at least 90% identity to amino acids 22-146 of SEQ ID NO:3 and comprising one or more substitutions thereto, wherein the amino acid T in position 112 is substituted; and
(2) an LGR4 binding region of a second R-spondin, the LGR4 binding region comprising an amino acid sequence having at least 90% identity to amino acids 21-138 of SEQ ID NO:4 and comprising one or more substitutions when compared to said sequence, wherein at least one of amino acids L, I, and I in positions 56, 58, and 63, respectively, is substituted; and
wherein the R-spondin variant has ZNRF3 and LGR4 binding activity.

3. A cell culture medium, comprising:
an R-spondin variant having ZNRF3 and LGR4 binding activity, the R-spondin variant comprising:
a ZNRF3 binding region of a first R-spondin, the ZNRF3 binding region comprising an amino acid sequence having at least 90% identity to amino acids 22-76 of SEQ ID NO:2 or to amino acids 22-78 of SEQ ID NO:3; and
an LGR4 binding region of a second R-spondin, the LGR4 binding region comprising an amino acid sequence having at least 90% identity to amino acids 72-138 of SEQ ID NO:4.

4. A cell culture medium, comprising:
an R-spondin variant having ZNRF3 and LGR4 binding activity, the R-spondin variant comprising:
(1) a ZNRF3 binding region of a first R-spondin, the ZNRF3 binding region comprising:
an amino acid sequence having at least 90% identity to amino acids 22-144 of SEQ ID NO:2 and comprising one or more substitutions thereto, wherein the amino acid T in position 111 is substituted; or
an amino acid sequence having at least 90% identity to amino acids 22-146 of SEQ ID NO:3 and comprising one or more substitutions thereto, wherein the amino acid T in position 112 is substituted; and
(2) an LGR4 binding region of a second R-spondin, the LGR4 binding region comprising an amino acid sequence having at least 90% identity to amino acids 21-138 of SEQ ID NO:4 and comprising one or more substitutions when compared to said sequence, wherein at least one of amino acids L, I, and I in positions 56, 58, and 63, respectively, is substituted.

5. A method of culturing cells responsive to an R-spondin, the method comprising the step of:

exposing a quantity of said cells to a cell culture medium containing an R-spondin variant, wherein the R-spondin variant has ZNRF3 and LGR4 binding activity and comprises:

(1) a ZNRF3 binding region of a first R-spondin, the ZNRF3 binding region comprising an amino acid sequence having at least 90% identity to amino acids 22-76 of SEQ ID NO:2 or to amino acids 22-78 of SEQ ID NO:3, and (2) an LGR4 binding region of a second R-spondin, the LGR4 binding region comprising an amino acid sequence having at least 90% identity to amino acids 72-138 of SEQ ID NO:4.

6. A method of culturing cells responsive to an R-spondin, the method comprising the step of:

exposing a quantity of said cells to a cell culture medium containing an R-spondin variant, wherein the R-spondin variant has ZNRF3 and LGR4 binding activity and comprises:

(1) a ZNRF3 binding region of a first R-spondin, the ZNRF3 binding region comprising:

an amino acid sequence having at least 90% identity to amino acids 22-144 of SEQ ID NO:2 and comprising one or more substitutions thereto, wherein the amino acid T in position 111 is substituted; or an amino acid sequence having at least 90% identity to amino acids 22-146 of SEQ ID NO:3 and comprising one or more substitutions thereto, wherein the amino acid T in position 112 is substituted; and (2) an LGR4 binding region of a second R-spondin, the LGR4 binding region comprising an amino acid sequence having at least 90% identity to amino acids 21-138 of SEQ ID NO:4 and comprising one or more substitutions when compared to said sequence, wherein at least one of amino acids L, I, and I in positions 56, 58, and 63, respectively, is substituted.

* * * * *

UNITED STATES PATENT AND TRADEMARK OFFICE
CERTIFICATE OF CORRECTION

PATENT NO. : 9,777,052 B2
APPLICATION NO. : 14/956921
DATED : October 3, 2017
INVENTOR(S) : Augen A. Pioszak It is certified that error appears in the above-identified patent and that said Letters Patent is hereby corrected as shown below:

In the Specification

Column 2, Line 1: After "affinities in the" delete "M" and replace with -- $\mu M$ --
Column 2, Line 57: Delete "pECso," and replace with -- $pEC_{50}$, --
Column 4, Line 18: Delete "158" and replace with -- I58 --
Column 5, Line 35: Delete "(1105" and replace with -- (I105 --
Column 5, Line 52: Delete "pK, pECso," and replace with -- $pK_I$, $pEC_{50}$, --
Column 13, Line 35: Delete "163M)" and replace with -- I63M) --
Column 18, Line 5: Delete "pECso" and replace with -- $pEC_{50}$ --
Column 19, Line 53: Delete "$pK_1$" and replace with -- $pK_I$ --
Column 20, Line 19: After "residues" delete "198," and replace with -- I98, --
Column 20, Line 27: After "L56 and" delete "158" and replace with -- I58 --
Column 20, Line 31: Delete "163M]triple" and replace with -- I63M]triple --
Column 21, Line 32: After "F62," delete "164," and replace with -- I64, --
Column 22, Line 4: After "F64," delete "166," and replace with -- I66, --

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*